(12) United States Patent
Schiedner et al.

(10) Patent No.: US 9,371,512 B2
(45) Date of Patent: Jun. 21, 2016

(54) METHOD FOR THE PRODUCTION OF PERMANENT HUMAN CELL LINES

(75) Inventors: Gudrun Schiedner, Cologne (DE); Christoph Volpers, Wiesbaden (DE)

(73) Assignee: CEVEC PHARMACEUTICALS GMBH, Cologne (DE)

( * ) Notice: Subject to any disclaimer, the term of this patent is extended or adjusted under 35 U.S.C. 154(b) by 0 days.

(21) Appl. No.: 13/147,775

(22) PCT Filed: Feb. 5, 2010

(86) PCT No.: PCT/DE2010/075012
§ 371 (c)(1),
(2), (4) Date: Oct. 14, 2011

(87) PCT Pub. No.: WO2010/094280
PCT Pub. Date: Aug. 26, 2010

(65) Prior Publication Data
US 2012/0040400 A1    Feb. 16, 2012

(30) Foreign Application Priority Data

Feb. 5, 2009   (DE) .................. 10 2009 003 439

(51) Int. Cl.
| | | |
|---|---|---|
| *C12N 15/85* | (2006.01) | |
| *C12N 5/10* | (2006.01) | |
| *C12P 21/00* | (2006.01) | |
| *C12N 5/073* | (2010.01) | |

(52) U.S. Cl.
CPC .............. *C12N 5/0605* (2013.01); *C12N 15/85* (2013.01); *C12N 2510/04* (2013.01); *C12N 2800/24* (2013.01)

(58) Field of Classification Search
CPC .. C12N 5/0605; C12N 15/85; C12N 2800/24; C12N 2510/04
See application file for complete search history.

(56) References Cited

U.S. PATENT DOCUMENTS

| | | | | |
|---|---|---|---|---|
| 5,631,158 | A * | 5/1997 | Dorai et al. ................. | 435/464 |
| 6,558,948 | B1 * | 5/2003 | Kochanek et al. ........... | 435/325 |
| 2007/0111312 | A1 * | 5/2007 | Schiedner et al. ........... | 435/455 |

FOREIGN PATENT DOCUMENTS

| | | |
|---|---|---|
| JP | 2003-514526 | 4/2003 |
| WO | WO 2007/056994 | 5/2007 |

OTHER PUBLICATIONS

Schiedner et al Human Gene Therapy, 2000, 2105-2116.*
Durocher et al Nucleic acid Research, 2002, 2e9, 1-9,.*
Jenkins et al American Journal of Medicine Genetics 38:416-417, 1991.*
Huang et al Journal of Neuroscience Methods, 2005, 159-166.*
Janabi et al Neuroscience Letter 195 (1995) 105-108.*
Tentori et al al International Journal of Oncology , 2005, 525-535.*
ATCC catalogue CRL1573 , 1-3.*
Schiedner et al BMC Biotechnol. Feb 12, 2008;8:13, 1-11.*
Wurm et al teach Nat. Biotechnol 2004, 22:1393-1398.*
Baldi et al., "Recombinant protein production by large-scale transient gene expression in mammalian cells: state of the art and future perspectives," *Biotechnol. Lett.*, 29(5):677-684, 2007.
Durocher et al., "High-level and high-throughput recombinant protein production by transient transfection of suspension-growing human 293-EBNA1 cells," *Nucleic Acid Research*, 30:e9, 2002.
Kunaparaju et al., "Epi-CHO, an episomal expression system for recombinant protein production in CHO cells," *Biotechnology and Bioengineering*, 91(6):670-677, 2005.
PCT International Preliminary Report on Patentability issued in International Application No. / PCT/DE2010/075012, dated Aug. 11, 2011.
Schiedner et al., "Efficient and reproducible generation of high-expressing, stable human cell lines without need for antibiotic selection," *BMC Biotechnology*, 8:13, doi:10.11861/1472-6750-8:13. 11 pages, 2008.
Schiedner et al., "Efficient transformation of primary human amniocytes by E1 functions of Ad5: Generation of new cell lines for adenoviral vector production," *Human Gene Therapy*, 11(15):2105-2116, 2000.
Office Action issued in Japanese Application No. 2011-548530, mailed Jun. 23, 2014.
Graham et al., "Characteristics of a human cell line transformed by DNA from human adenovirus type 5", *J Gen Virol.*, 36(1):59-74, 1977.

* cited by examiner

*Primary Examiner* — Anoop Singh
(74) *Attorney, Agent, or Firm* — Parker Highlander PLLC

(57) ABSTRACT

The present invention relates to a permanent human cell line comprising a nucleic acid sequence for the adenoviral gene functions E1A and E1B and the nucleic acid sequence for the SV40 large T-antigen or the Epstein-Barr virus (EBV) nuclear antigen 1 (EBNA-1). Further, the present invention relates to a method for transient expression of recombinant polypeptides and proteins in said permanent human cell line.

8 Claims, 11 Drawing Sheets

METHOD FOR THE PRODUCTION OF PERMANENT HUMAN CELL LINES

This application is a national phase application under 35 U.S.C. §371 of International Patent Application No. PCT/DE 2010/075012 filed Feb. 5, 2010 which claims priority to German Patent Application No. 10 2009 003 439.0 filed Feb. 5, 2009. The entire text of the above-referenced disclosures are specifically incorporated herein by reference without disclaimer.

The present invention relates to a permanent human cell line comprising a nucleic acid sequence for the adenoviral gene functions E1A and E1B and the nucleic acid sequence for the SV40 large T-antigen or the Epstein-Barr virus (EBV) nuclear antigen 1 (EBNA-1). Further, the present invention relates to a method for transient expression of recombinant polypeptides and proteins in said permanent human cell line.

Beside bacteria, yeasts, and plant cells, in particular animal cells, are used for the production of recombinant polypeptides and proteins. Today, about 60-70% of all therapeutic proteins are produced in mammalian cells (Wurm, Nat. Biotechnology 22, 1393-1398, 2004). The production of recombinant polypeptides or proteins in cell culture, i.e. in vitro, for therapeutic, diagnostic or technical purposes can generally be effected by two different ways. In stable, durable or permanent established cell lines the nucleic acid encoding the desired polypeptide or protein is integrated into the chromosomal DNA of the cell with at least one copy and is passed together with the cellular chromosome set to daughter cells in cell division (so called stable expression in production cell lines). For the production of these stable production cell lines it is necessary that at least one of the nucleic acids introduced into the cell by transfection carries a gene function providing an advantage in terms of selection in cell culture during growth. The nucleic acid having such a gene function is not necessarily on the same molecule as the expression cassette for the desired polypeptide or protein. Said gene function is either an antibiotic resistance gene or a resistance gene against chemotherapeutic agents in the media (e.g. often used for mammalian cells; Wurm, Nat. Biotechnology 22, 1393-1398, 2004), a gene having a gene product complementing a deficient metabolic pathway (e.g. used in yeast cells), or a transforming gene function (shown for human amniocytic cells; Schiedner et al., BMC Biotechnology 8, 13, 2008). In this way, it is ensured that such cells having a stable integration of the transfected nucleic acid into the chromosomal DNA of the cell and producing said gene product overgrow other cells without such integration and can be selected. In preparing production cells by transfection in the so called host cell line on the one hand the nucleic acid encoding the recombinant polypeptide (the so called transgene) is transferred together with the necessary transcriptional regulation elements and on the other hand a second expression cassette is transferred having a gene encoding a selection marker whose gene product provides a certain advantage in terms of selection. A few days after gene transfer during which the cells are cultured, e.g. in a culture medium without selection reagent, a suitable selection reagent is added to the medium. In the presence of said selection reagent only those cells having integrated the nucleic acids used for transfection and expressing the selection marker survive and grow. Commonly used selection markers are the neomycin resistance gene, the hygromycin resistance gene and the dihydrofolate reductase (DHFR) (Wurm, Nat. Biotechnology 22, 1393-1398, 2004; Wurm and Jordan, 309-333 in: Makrides (Hrsg.), Gene Transfer and Expression in Mammalian Cells, Elsevier, Amsterdam, 2003). Accordingly, the selection is carried out in culture medium with selection reagents such as the antibiotics neomycin or hygromycin and the synthetic glucocorticoid methotrexate, respectively. Generally, cells having the selection marker and the transgene, surviving the process of selection and proliferating (so called transformants) are subsequently singularized (cloned) to ensure that all cells in the culture are genetically identical and to separate the desired production cells lines having the best production rate from less well producing cell lines.

In contrast, for the so called transient expression the nucleic acid introduced into the cell by transfection and encoding the desired polypeptide or protein is not integrated into the chromosomal DNA of the cell and is not selected to this result, respectively. Thus, the introduced nucleic acid is generally thinned out and gets lost in the course of cell division during growth in culture. This presupposes the temporary, transient nature of this expression method. The selection of stable production cell lines with good expression efficiency lasts some months and raises serious costs. In contrast, amounts of milligram of the desired polypeptide or protein can be produced within a few days by transient expression. Speed and costs are essential factors for the industrial development of biopharmaceutical and diagnostic products. The transient expression of proteins in small amounts or of different protein variants is therefore carried out beside fundamental research for the early explorative and preclinical development, e.g. for target identification, assay development, biochemical characterization of gene products, for the toxicology and for pharmacokinetic as well as pharmacodynamic investigations (Baldi et al., Biotechnol. Lett. 29, 677-684, 2007; Pham et al., Molecular Biotechnology 34, 225-237, 2006). In contrast, the industrial production of proteins in scale of grams up to kilograms for the performance of larger clinical studies and the market supply is performed by stable production cell lines.

For example, in EP 1948789 a method for the production of a permanent human amniocytic cell line by transfection of a cell transforming factor without the use of a selection marker is described.

So far, secreted, membrane-bound and intracellular proteins could be produced by transient gene expression. Currently, mammalian cells are the commonly used expression systems for a lot of complex proteins, in particular if said proteins should be used for therapeutic purposes, since prokaryotic and simple eukaryotic cell systems (e.g. yeasts) are clearly disadvantaged in respect of posttranslational modifications. So far, four mammalian cell lines have basically been used for transient protein expression: COS-1 and COS-7 cells, respectively, deriving from the CV-1 cell line derived from kidney cells of the African green monkey; BHK cells deriving from baby hamster kidney cells; CHO cells deriving from the ovary of the Chinese hamster; and HEK293 cells, a human embryonic kidney cell line having neuronal characteristics (Pham et al., Molecular Biotechnology 34, 225-237, 2006; Wurm et Bernard, Current Opinion in Biotechnology 10, 156-159, 1999). The transient expression in mammalian cell lines is generally based on the transfection of a plasmid vector incorporating the expression cassette with the sequence encoding the desired gene product. Also viral expression vectors such as Semliki Forest virus or adenovirus can be used but they are uncommon since they are efficient but time-consuming and connected with high safety requirements. A plurality of physical and chemical methods has been developed for the DNA transfer in cultivated mammalian cells. Physical methods for gene transfer comprise electroporation, nucleofection and micro injection. For using chemical transfection methods one uses inorganic substances (e.g. calcium phosphate/DNA co-precipitation), cationic polymers (e.g. polyethylenimine, DEAE-dextran method) or cationic lipids (so called lipofection). Calcium phosphate and polyethylenimine are the most commonly used reagents for transfection for nucleic acid transfer in larger scales (up to several liters) (Baldi et al., Biotechnol. Lett. 29, 677-684, 2007).

The described methods for transient expression of polypeptides and proteins based on cells lines being known for a long time have disadvantages for a number of reasons. Low expression efficiencies are one problem in connection with transient methods. For improving the cellular expression yields different genetic systems have been used for increasing the number of gene copies per cell by means of episomal replication of the introduced nucleic acid. COS cells express the large T-antigen of simian virus 40 (SV40), a replication factor effecting an episomal replication to a high number of plasmid copies carrying a SV40 replication origin (SV40 ori). Initial event of said replication is the binding of the T-antigen to the SV40 replication origin (SV40 ori) whereby cellular replication factors are recruited to the DNA/T-antigen complex and a replication is induced by cellular DNA polymerase. Two genetic variants of the HEK293 cell line being generated by transformation of human embryonic kidney cells with sheared adenovirus type 5 DNA about 30 years ago and being well tranfectable have been described. Said variants also express said large T-antigen of SV40 (HEK293T) and said Epstein-Barr virus (EBV) nuclear antigen 1 (EBNA-1) (HEK293E or 293EBNA-1), respectively. Said cell lines should provide an episomal replication or amplification of plasmids having a SV40-ori and an EBV-oriP, respectively. The replication factor EBNA-1 interacts in the latter case with the replication origin oriP of EBV. At least for HEK293E cells an increase of the expression yields has been detected by using oriP containing expression plasmids. In contrast to the use of EBNA-1 in combination with the replication origin oriP, some studies indicate that no strong replication of plasmids having SV40-ori occurs in HEK293T cells (Durocher et al., Nucleic Acid Research 30, e9, 2002). A stable variant of CHO cells have been generated, which expresses the large T-antigen (LT) of polyomavirus (Epi-CHO) and which can be used in combination with a plasmid carrying the replication origin of polyomavirus (PyOri) (Kunaparaju et al., Biotechnology and Bioengineering 91, 670-677, 2005). Yields averaged of about 10-20 mg/liter are generated by said transient expression of recombinant proteins by using such mammalian cell systems (Baldi et al., Biotechnol. Lett. 29, 677-684, 2007). In contrast, yields in the range of several grams per liter are normal by using stable, permanent production cell lines, as mentioned above, however, with a quite significant higher expense of time and money.

A further disadvantage of cell systems used for recombinant protein expression so far is that some cell lines are indeed suitable for transient expression due to their ability to be easily transfected and to allow episomal plasmid amplification (e.g. HEK293T or HEK293E cells), but other cell lines are preferably used for the production of stable cell lines due to their properties in cultivation and yields (e.g. CHO cells). However, since cell systems differ from each other in several aspects of posttranslational modification, data of structure and function of said gene products obtained for a specific cell system after transient expression (mostly in an earlier phase of the development of therapeutic protein products) can only be transferred in a highly limited way to the structure and function of said gene products after expression in stable cell lines of a distinct cell system (mostly in the later phase of development, for clinical studies and market supply). Posttranslational modifications, such as glycosylation, phosphorylation, carboxylation, palmitoylation or specific cleavages are of great importance for different properties of the expression products for many candidates of therapeutic products. They can have an influence on the activity, solubility, half life, stability or immunogenicity. Thus, human cell systems play an increasingly rule for the production of therapeutic proteins; only human cells as production facilities provide an authentic, human modification of the expression products and reduce therefore the risk of affected product quality or undesired side affects. It is for example known for recombinant erythropoietin being applied therapeutically in humans that protein produced in CHO cells (Epoetin Alpha) exhibits in its carbohydrate side chains moieties of N-glycolylneuraminic acid while the protein produced in human cells (Epoetin Delta)—just like natural human erythropoietin—does not contain such sugar moieties. Given the fact that the human being demonstrably forms circulating antibodies against said "foreign" sugar structures the use of a human expression system seems to be favorably (Varki, Am. J. Phys. Anthropol. 33, 54-69, 2001). Currently, there is no human cell system available being comparably well suited for transient expression and the production of stable production cell lines and thus providing a reproducible product profile over the whole development of a protein based therapeutic.

Human cells are particularly well suited for the production of human biotherapeutics since they express complex polypeptides—in contrast to other mammalian cells or animal cells—with authentic posttranslational modification pattern. The glycosylation pattern of complex recombinant proteins, so the structure and arrangement of sugar moieties in the molecule, will reproduce the pattern of the authentic human polypeptide substantially better in the production in human cells than in the production in non human production systems. Said glycosylation pattern is often of crucial importance for important properties of the polypeptide such as biological activity, stability, solubility and immunogenicity.

Thus, the object of the invention is the provision of a human cell system being comparably well suited for the transient expression of polypeptides and the production of stable production cell lines.

Said object is solved by the subject matter as defined in the claims.

The following figures illustrate the invention.

FIGS. 1a-1c show schematically the assembly of plasmids for permanent expression of T-antigen. In pGS158 (FIG. 1a) T-antigen is expressed under the control of the human CAG promoter (a hybrid promoter of the immediate-early enhancer of the human cytomegalovirus and a modified chicken β-actin promoter with the first intron) (Niwa et al., Gene 108:193-199, 1991), in pGS159 (FIG. 1b) under control of the RSV (Rous sarcoma virus) promoter (Makrides, 9-26 in: Makrides (Hrsg.), Gene Transfer and Expression in Mammalian Cells, Elsevier, Amsterdam, 2003) and in pGS161 (FIG. 1c) under control of the human CMV (cytomegalovirus) promoter (Makrides, 9-26 in: Makrides (Hrsg.), Gene Transfer and Expression in Mammalian Cells, Elsevier, Amsterdam, 2003).

FIGS. 2a-2c show schematically the assembly of plasmids for the transient expression of the human alpha 1-antitrypsin (hAAT) and human erythropoietin (Epo), respectively, each under control of the human CMV promoter. Plasmid pGS116 (FIG. 2a) and pGS151 (FIG. 2b) contains identical expression cassettes for hAAT, pGS151 additionally contains the origin of the DNA replication of simian virus 40 (SV40 ori). pGS177 contains the SV40 on in addition to the Epo expression cassette as well (FIG. 2c).

FIG. 3 shows schematically the amount of hAAT in the culture supernatant transiently expressed in different amniocytic cell lines expressing T-antigen (CAP-T Z582, Z583 and Z597) in comparison to the parental amniocytic cell line (CAP) without T-antigen expression. In Z582 the T-antigen is expressed under control of the CAG promoter (Niwa et al., Gene 108:193-199, 1991), in Z583 under control of the RSV (Rous sarcoma virus) promoter (Makrides, 9-26 in: Makrides (Hrsg.), Gene Transfer and Expression in Mammalian Cells, Elsevier, Amsterdam, 2003) and in Z597 under control of the CMV (cytomegalo) promoter (Makrides, 9-26 in: Makrides (Hrsg.), Gene Transfer and Expression in Mammalian Cells, Elsevier, Amsterdam, 2003).

Figure 1A:
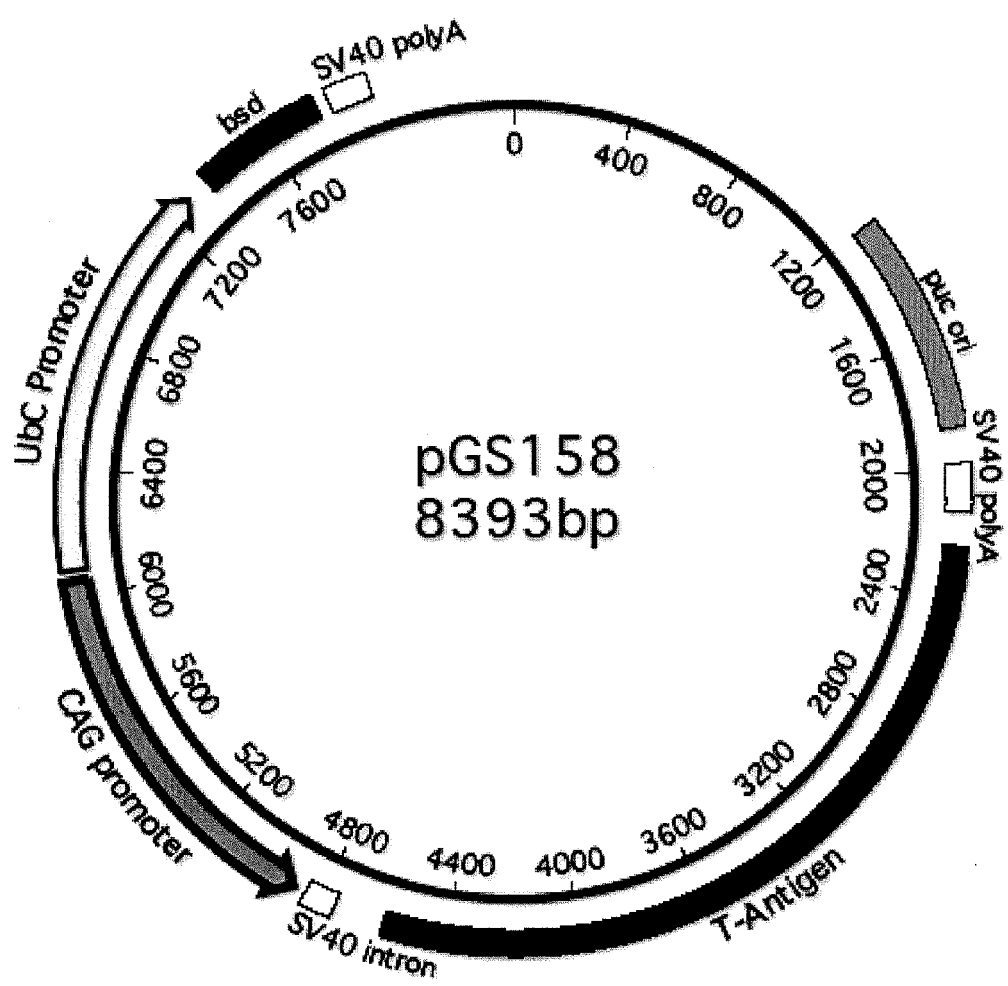
Figure 1B:
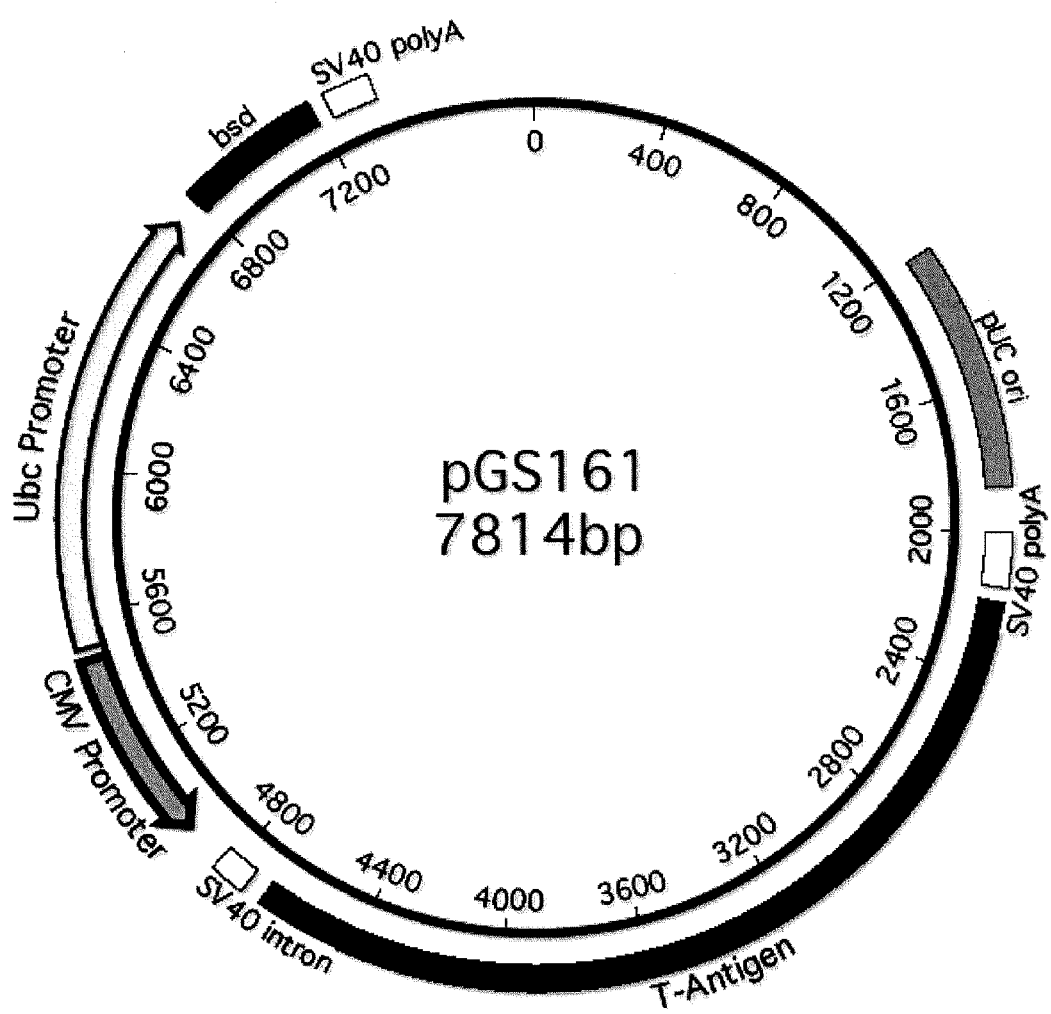
Figure 1C:
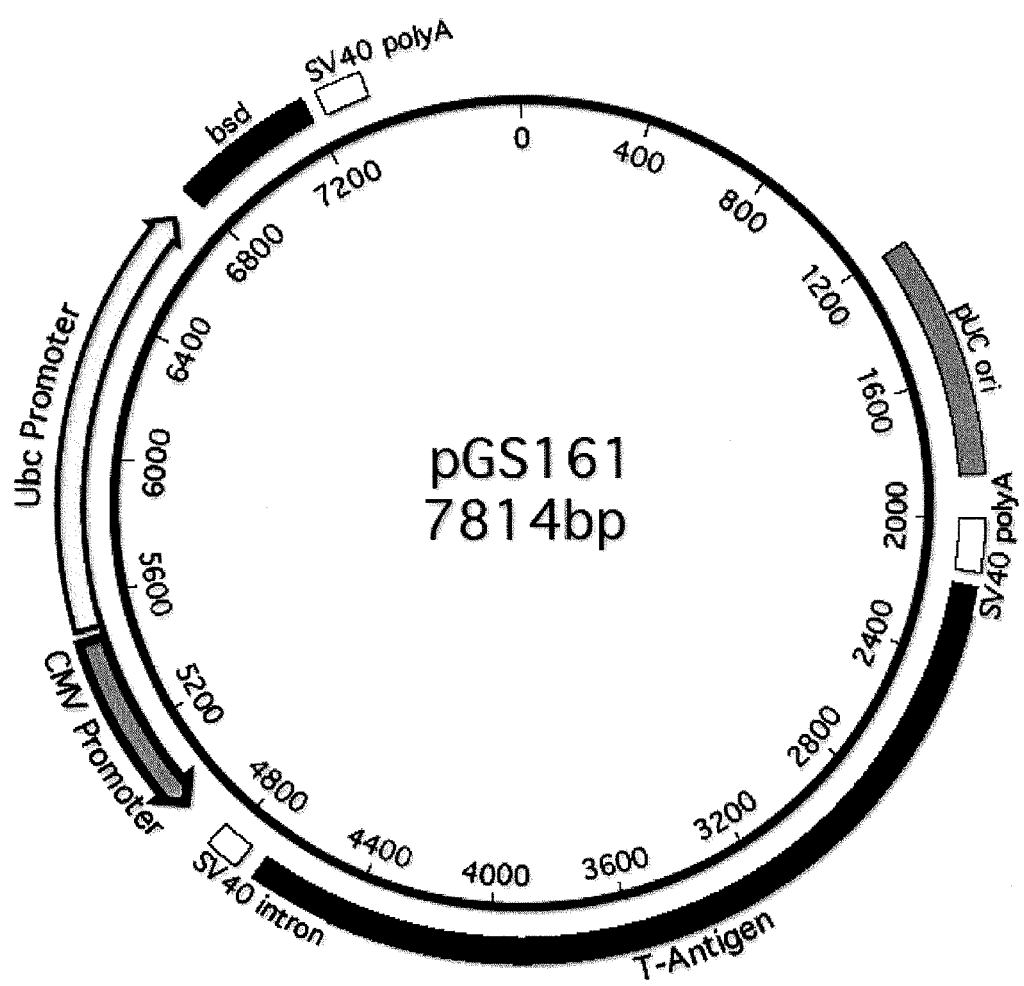

The term "amniocytes", as used herein, relates in the broadest sense to all cells that are present in amniotic liquor and may be obtained by amniocentesis. They originate either from amnion or from fetal tissue that is in contact with the amniotic liquor. Three main classes of amniocytes have been described that can be distinguished based on morphological criteria: fibroblast like cells (F cells), epitheloid cells (E cells) and amniotic fluid cells (amniotic fluid cells, AF cells) (Hohn et al., Pediat. Res. 8:746-754, 1974). AF cells are the predominant cell type.

The term "expression cassette" relates particularly to a nucleic acid molecule and a region of a nucleic acid molecule, respectively, containing a regulatory element or promoter being positioned in front of the coding region, a coding region and an open reading frame, respectively, as well as a transcriptional termination element lying behind the coding region. The regulatory element and the promoter, respectively, residing in front of the coding region, can be a constitutive, i.e., a promoter permanently activating the transcription (e.g. CMV promoter), or a regulatable promoter, i.e. a promoter which can be switched on and/or off (e.g., a tetracycline regulatable promoter). The coding region of the expression cassette can be a continuous open reading frame as in the case of a cDNA having a start codon at the 5' end and a stop codon at the 3' end. The coding region can consist of a genomic or a newly combined arrangement of coding exons and interspersed non-coding introns. However, the coding region of the expression cassette can consist of several open reading frames, separated by so called IRES (Internal Ribosome Entry Sites).

The term "permanent cell lines", as used herein, relates to cells being genetically modified in such a way that they may continue to grow permanently in cell culture under suitable culture conditions. Such cells are also called immortalized cells.

The term "polypeptide" or "recombinant polypeptide", as used herein, relates to peptides consisting of at least 2 amino acids. The polypeptide can be modified co- and/or post-translationally, e.g., by the attachment of sugar residues or by modification of amino acid residues. The polypeptide can be linear, circular or branched. Furthermore, the polypeptide can consist of more than one amino acid chain, wherein the chains may adopt more or less complex three-dimensional structures by intra- and/or intermolecular bonds (e.g., secondary, tertiary, quaternary structure). If the polypeptide consists of one amino acid chain it can adopt more or less complex three-dimensional structures also by intramolecular bonds. The polypeptides can be pharmacologically or immunologically active polypeptides or polypeptides used for diagnostic purposes.

The term "primary cells", as used herein, relates to cells that were obtained by direct removal from an organism or a tissue and put in culture. Primary cells exhibit only a very limited life span.

The term "production cell lines", as used herein, relates to permanent cell lines that were genetically stable modified by the introduction of a transgene encoding the desired polypeptide to be produced.

The term "CAP", as used herein, relates to a permanent human amniocytic cell line generated by immortalization of primary human amniocytes with adenoviral gene functions E1A and E1B.

The term "CAP-T", as used herein, relates to CAP-cells that are in addition stably transfected with a nucleic acid molecule containing the sequence of the SV40 large T-antigen.

The term "transfection", as used herein, relates to any method suitable for the introduction of the mentioned nucleic acid(s) into the cells. As examples the classical calcium phosphate method, electroporation, liposomal systems of any kind and combinations of these methods are to be mentioned.

The term "transient expression" as used herein, relates to any method in which nucleic acid(s) are introduced into the cell by transfection without the selection of stable cell lines by a suitable selection method, said stable cell lines can be onwards cultured in cell culture permanently.

The term "stabile expression", as used herein, relates to the expression of a transgene in production cell lines.

The term "transgene", as used herein, relates to the nucleic acid sequence encoding a recombinant polypeptide.

A subject matter of the present invention relates to a method for producing a permanent human cell line comprising the following steps:
  a) Transfecting primary human cells with a nucleic acid molecule comprising a nucleic acid sequence encoding the adenoviral gene functions E1A and E1B; so called 1. transfection, and
  b) subsequently transfecting the permanent human cell line with a nucleic acid molecule comprising a nucleic acid sequence encoding the SV40 large T-antigen, so called 2. transfection.

Preferably, said nucleic acid molecule of step b) of the method for the production of a permanent human cell line according to the present invention comprises a nucleic acid sequence encoding a non secreted form of the SV40 large T-antigen.

During the transfection in step b) of the method according to the present invention the permanent human cell line is alternatively transfected with a nucleic acid molecule comprising a nucleic acid sequence encoding the Epstein-Barr virus (EBV) nuclear antigen 1 (EBNA-1), so called 2. transfection. Preferably, said nucleic acid molecule comprises a nucleic acid sequence encoding a non secreted form of the Epstein-Barr virus (EBV) nuclear antigen 1 (EBNA-1).

By the transfections performed in the method according to the present invention said primary human cells are preferably transfected stably, i.e. the transfected DNA is integrated into the genome of the cell.

The cells are immortalized by the transfection of said primary human cells with the nucleic acid molecule comprising the nucleic acid sequences encoding E1A and E1B. The nucleic acid molecule used for the immortalization of said primary human cells comprises nucleic acid sequences of E1A and E1B preferably deriving from human adenoviruses, in particular of human adenovirus serotype 5. In a preferred embodiment the nucleic acid molecule used for the immortalization comprises the nucleic acid sequence encoding the adenoviral gene function pIX in addition to the nucleic acid sequences encoding E1A and E1B. The pIX polypeptide, a viral structural protein, acts as a transcriptional activator on different viral and cellular promoters such as the thymidine kinase and the beta-globin promoter. An exemplary sequence can be found in GenBank acc. no. X02996. In particular, nucleic acid molecules comprise nucleotides 1 to 4344 (SEQ ID NO:1 comprises nucleic acid sequences encoding E1A, E1B and pIX), 505 to 3522 (SEQ ID NO:2 comprises nucleic acid sequences encoding E1A and E1B) or the nucleotides 505 to 4079 (SEQ ID NO:3 comprises nucleic acid sequences encoding E1A, E1B and pIX) of human adenovirus serotype 5.

In particular, the human cells are transfected with the nucleic acid sequences encoding the desired gene function, which is to be expressed, in form of an expression cassette. Said expression cassette comprises a nucleic acid molecule containing a regulatory element or promoter being positioned in front of the coding region, a coding region and an open reading frame, respectively, as well as a transcriptional termination element lying behind the coding region.

In particular, in one embodiment the expression cassette or the nucleic acid molecule contains a nucleic acid sequence for the SV40 large T-antigen (SEQ ID NO: 4), the nucleic acid sequence for a promoter selected from the groups of CMV Promoter (SEQ ID NO:5), CAG promoter (Niwa et al., Gene 108:193-199, 1991) and RSV promoter (GenBank acc. no. DQ075935), the sequence for SV40 SD/SA (intron) (SEQ ID NO:6) and the nucleic acid sequence for SV40 polyA (SEQ ID NO:7).

In a further embodiment, the expression cassette or the nucleic acid molecule contains in particular a nucleic acid sequence for the Epstein-Barr virus (EBV) nuclear antigen 1 (EBNA-1) (SEQ ID NO:8), the nucleic acid sequence for a promoter selected from the group of CMV promoter (SEQ ID NO:5), CAG promoter (Niwa et al., Gene 108:193-199, 1991) and RSV promoter (GenBank acc. no. DQ075935), the nucleic acid sequence for SV40 SD/SA (intron) (SEQ ID NO:6) and the nucleic acid sequence for SV40 polyA (SEQ ID NO:7).

The primary human cells are obtained by direct removal from the organism or a tissue removed from the organism and put in culture. Preferred are such primary human cells, which can be well turned into permanent human cell lines by expression of adenoviral E1A and E1B, in particular amniocytic cells, embryonic retina cells and embryonic cells of neuronal origin.

Preferably permanent human amniocytic cell lines are produced by the method according to the present invention.

The method of the present invention can also be performed with already existing immortalized human cell lines instead of step a), in particular with already existing immortalized human amniocytic cell lines having the nucleic acid sequences for the adenoviral gene functions E1A and E1B in their genome. Preferably, the immortalized human cell lines comprise the nucleic acid sequences for the adenoviral gene functions E1A, E1B and pIX in their genome. The existing immortalized human cell lines, in particular immortalized human amniocytic cell lines, are transfected on demand with the above mentioned nucleic acid molecule containing an expression cassette encoding the SV40 large T-antigen or the Epstein-Barr virus (EBV) nuclear antigen 1 (EBNA-1). The person skilled in the art recognizes that the 2. transfection is in respect to its time only dependent on the 1. transfection of the primary human cell in that it has to be performed after the 1. transfection. It is not necessary that the 2. transfection takes place immediately after the 1. transfection. Thus, also immortalized human cell lines being immortalized with E1A and/or E1B and being established since several years can be transfected on demand with the above mentioned nucleic acid molecule in a 2. transfection. Preferably, immortalized human amniocytes, immortalized human embryonic retina cells, in particular PER.C6 cells, or immortalized human embryonic cells of neuronal origin, in particular HEK 293 cells, can be used for this.

A subject matter of the present invention refers to a permanent human cell line comprising a nucleic acid sequence for the adenoviral gene functions E1A and E1B and a nucleic acid sequence for SV40 large T-antigen or the Epstein-Barr virus (EBV) nuclear antigen 1 (EBNA-1). Preferably, the present invention relates to a permanent human cell line comprising the nucleic acid sequence for the adenoviral gene functions E1A, E1B and pIX and the nucleic acid sequence for SV40 large T-antigen or the Epstein-Barr virus (EBV) nuclear antigen 1 (EBNA-1). More preferably, the present invention relates to a permanent human amniocytic cell line comprising the nucleic acid sequences for the adenoviral gene functions E1A and E1B and the nucleic acid sequence for the SV40 large T-antigen or the Epstein-Barr virus (EBV) nuclear antigen 1 (EBNA-1). Most preferably, the present invention relates to a permanent human amniocytic cell line comprising the nucleic acid sequence for the adenoviral gene functions E1A, E1B and pIX and the nucleic acid sequence for the SV40 large T-antigen or the Epstein-Barr virus (EBV) nuclear antigen 1 (EBNA-1).

In particular, a further subject matter of the present invention relates to a permanent human cell line, preferably a permanent human amniocytic cell line, obtained by use of the method according to the present invention.

A further subject matter of the present invention relates to a method for transient expression of recombinant polypeptides or proteins by use of the permanent human cell line according to the present invention, wherein said method comprises the following steps:

a) Transfecting said permanent human cell line with a nucleic acid molecule comprising a nucleic acid sequence encoding the desired recombinant polypeptide or protein and a recognition or binding site for SV40 large T-antigen or the Epstein-Barr virus (EBV) nuclear antigen 1 (EBNA-1), b) Culturing the transfected permanent human cell line obtained in step a) under conditions allowing the expression of said desired recombinant polypeptide or protein, and subsequently c) Isolating said desired recombinant polypeptide or protein from the cells or from the culture supernatant.

A preferred embodiment of the present invention relates to a method for transient expression of recombinant polypeptides or proteins under use of the permanent human amniocytic cell line according to the present invention, wherein said method comprises the following steps:
  a) Transfecting said permanent human amniocytic cell line with a nucleic acid molecule comprising a nucleic acid sequence encoding the desired recombinant polypeptide or protein and a recognition or binding site for SV40 large T-antigen or the Epstein-Barr virus (EBV) nuclear antigen 1 (EBNA-1),
  b) Culturing the transfected permanent human amniocytic cell line obtained in step a) under conditions allowing the expression of said desired recombinant polypeptide or protein, and subsequently
  c) Isolating said desired recombinant polypeptide or protein from the cells or from the culture supernatant.

If the permanent human cell line according to the present invention contains a nucleic acid molecule comprising the nucleic acid sequence encoding the SV40 large T-antigen, the cell line is e.g. transfected with an expression plasmid containing an expression cassette or a nucleic acid molecule comprising a nucleic acid sequence encoding the transgene to be expressed and the SV40 replication origin (SV40 ori). The SV40 large T-antigen being stably expressed intracellularly in the cell line binds to the SV40 replication origin of the expression plasmid being introduced by transfection into the cell line and causes an episomal replication of the expression plasmid and thus an amplification of the copy number of the transgene to be expressed. The desired gene product encoded by the transgene can be obtained from the cells or from the culture supernatant after the cells have been cultivated for a few days. Thus, said transgene is expressed transiently.

If the permanent human cell line according to the present invention contains a nucleic acid molecule comprising the nucleic acid sequence encoding the Epstein-Barr virus (EBV) nuclear antigen 1 (EBNA-1), the cell line is e.g. transfected with an expression plasmid comprising an expression cassette or a nucleic acid molecule comprising a nucleic acid sequence encoding the transgene to be expressed and the EBV replication origin (EBV oriP) (Durocher et al., Nucleic Acids Research Vol. 30 Nr. 2 e9, 2002; Tuvesson et al. Cytotechnology 56:123-136, 2008). The EBNA-1 of EBV being stably expressed intracellularly in the cell line binds to the oriP replication origin of the expression plasmid being introduced by transfection into the cell line and causes an episomal replication of the expression plasmid and thus an amplification of the copy number of the transgene to be expressed. The desired gene product encoded by the transgene can be obtained from the cells or from the culture supernatant after the cells have been cultivated for a few days. Thus, said transgene is expressed transiently.

The cells according to the present invention can be cultured under usual conditions for the cultivation of eukaryotic cells at about 37° C., 95% humidity and 8% $CO_2$. The cells according to the present invention can be cultured in serum containing or serum free medium, in adherent culture or in suspension culture. The cultivation in suspension can take place in diverse fermentation vessels, e.g. in stirred tank reactors, wave reactors, in shaker vessels or spinner vessels or in so called roller bottles. Thus, the cells are suitable for a scale up process into the industrial scale. The transfection of the cells for transient expression can take place with the diverse transfection methods as mentioned above. Transfection and transient expression can also be performed in the high throughput format and screening, respectively, e.g. in a 96 or 384 well format.

T-antigen of simian virus 40 (SV40) is a multifunctional phosphoprotein controlling both the viral replication and the cellular functions after infection. T-antigen is a transforming agent and interferes in the cell cycle via interaction with the tumor suppressor protein p53. During replication of the viral genome the T-antigen is necessary as DNA helicase for wresting the double-stranded genome. T-antigen is the only viral protein being necessary for the replication. The other functions are fulfilled by cellular proteins. In the first step of DNA replication 12 T-antigen molecules bind to the origin of the DNA replication (ori) in the SV40 genome as double hexamers. Subsequently, the necessary cellular proteins such as DNA polymerase bind to said helicase complex and wrest and replicate the DNA. The so called "minimale ori" consists of a core sequence being 63 bp in length. No integration into the host genome occurs in a transient transfection of circular plasmids into the target cell. This result in that the plasmid concentration decreases steadily after cell division and the expression of a gene lying on the encoding plasmid is only temporarily. The introduction of the SV40 ori-fragment into the expression plasmid and the expression of the SV40 T-antigen in the production cell line result in an increased copy number of the plasmid and thus in an increased expression efficiency.

The method for transient expression of polypeptides and proteins according to the present invention has the advantage that it is more efficient in view of the quantity and quality of the recombinant gene product and thus it is also more cost effective in the whole process of industrial development of protein based therapeutics than methods used so far. In particular, it is of advantage that a highly efficient transient expression system is provided on the basis of a human cell line, which firstly modifies human proteins posttranslational authentically in contrast to non human mammalian cells and non mammalian cells and which secondly is comparably well suited for the establishment of stable production cell lines in the industrial production process. By this it can be ensured that in the course of the development of diagnostic and therapeutic products qualitative features of the gene product after transient expression in the early stage of development and after stable expression in permanent production cell lines in the late phase and industrial production have the greatest possible identity, in particular in respect of differences in the features, which may be caused by the nature of the cell systems.

A further advantage of the present invention is that the permanent human cell lines according to the present invention exhibit a high expression yield by transient expression. So, surprisingly very high production yields of up to 60 mg/liter have been found in the culture supernatant in transient expression in amniocytic cell lines producing SV40 T-antigen after transfection with a plasmid vector having in addition to the sequence coding for the desired gene product a SV40 replication origin (SV40 ori). Said production yields have been more than 70 times higher than in transient expression in an amniocytic cell line expressing no T-antigen.

A further advantage of said permanent human cell line according to the present invention is that a human cell system is provided, preferably based on immortalized human amniocytes, which is suitable both for the transient expression of proteins and the stable expression of proteins in permanent production cell lines (Schiedner et al., BMC Biotechnology 8, 13, 2008). Compared to the use of different cell systems for the transient expression (e.g. HEK293 or HEK293 variants) and the stable expression (e.g. CHO) the risk is minimized that structural and functional properties of the expression products from transient and stable production differ from each other, if said structural and functional properties are based on the nature of the expression system. Thereby, the planning of the development process is improved and the development process is less time intensive and more cost effective.

Nucleic acid sequences for the expression of the at least one recombinant polypeptide are contained in at least one expression cassette. Said expression cassettes contain promoters and transcriptional termination sequences. CMV (cytomegalovirus) promoter (Makrides, 9-26 in: Makrides (Hrsg.), Gene Transfer and Expression in Mammalian Cells, Elsevier, Amsterdam, 2003), EF-1α promoter (Kim et al., Gene 91:217-223, 1990), CAG promoter (a hybrid promoter of the immediate-early enhancer of the human cytomegalovirus and a modified chicken β-actin promoter with first intron) (Niwa et al., Gene 108:193-199, 1991), human or murine pgk (phosphoglycerate kinase) promoter (Adra et al., Gene 60:65-74, 1987), RSV (Rous sarcoma virus) promoter (Makrides, 9-26 in: Makrides (Hrsg.), Gene Transfer and Expression in Mammalian Cells, Elsevier, Amsterdam, 2003) or SV40 (simian virus 40) promoter (Makrides, 9-26 in: Makrides (Hrsg.), Gene Transfer and Expression in Mammalian Cells, Elsevier, Amsterdam, 2003) may serve for example as promoters. The polyadenylation sequences of the SV40 large T-antigen (GenBank acc. no. J02400) or the human G-CSF (granulocyte colony stimulating factor) gene (Mizushima and Nagata, Nucl. Acids Res. 18:5322, 1990) may serve for example as polyadenylation sites.

A further subject matter of the present invention relates to the polypeptide or protein obtained by use of the method according to the present invention.

The recombinant polypeptide of the method according to the present invention may be a therapeutic protein such as human alpha 1-antitrypsin or growth factors such as erythropoietin or interleukin-2. Human alpha 1-antitrypsin (hAAT) is a proteinase inhibitor which inhibits elastase and other proteinases and which is therapeutically active in the case of inherited hAAT deficiency leading to severe damages of the lung and the liver. Erythropoietin is an important growth factor for erythrocytes (red blood cells) that has a blood forming activity in the case of anemia as well as in the case of transplantation patients. Interleukin-2 (Il-2) is a cellular messenger of the immune system and is of significant importance in the activation of the cellular immune response, for example in the case of tumor diseases. Blood clotting factors, such as factor VIII and IX used in the case of hemophilia patients having blood clotting disorders, also belong to the therapeutically active polypeptides. The recombinant polypeptide of the method according to the present invention may be a hormone. Biotechnologically engineered hormones are used in the substitution therapy in patients having hormonal disorders. Examples are the blood sugar lowering hormone insulin, upon which many patients having diabetes mellitus are dependent, somatotropin (growth hormone) for the treatment of dwarfism, and gonadotrope factors such as the follicle stimulating hormone (FSH) or luteinising hormone (LH) for the treatment of fertility disorders. Furthermore, the recombinant polypeptide can be an enzyme modifying posttranslationally other recombinant polypeptides being expressed intracellularly or in the culture supernatant simultaneously e.g. an enzyme involved in glycosylation. The gene products E1A, E1B and pIX expressed in the permanent human cell line according to the present invention as well as the SV40 large T-antigen and the Epstein-Barr virus (EBV) nuclear antigen 1 (EBNA-1) do not belong to the desired polypeptide to be produced.

The recombinant polypeptide of the method according to the present invention can be a recombinant antibody which may be used for therapeutic or diagnostic purposes. Antibodies against the tumor necrosis factor alpha (TNF-α) are used in the case of patients with rheumatoid arthritis, antibodies against the cellular receptor of the epidermal growth factor (EGFR) are used in the case of cancer patients. Antibodies used for diagnostic purposes may be for example components of commercial diagnosis kits based on methods such as the enzyme-linked immunosorbent assay (ELISA) or the radio immunosorbent assay (RIA). In these test assays, the antibodies serve for the detection of the antigens of infectious agents such as the human hepatitis B virus.

Antibodies or immunoglobulins (Ig) consist of a heavy and a light chain each consisting of variable and constant regions or domains. The nucleic acid sequences of the transfected nucleic acid molecules for the expression of an antibody may contain two separated expression cassettes, one of which encoding the light chain and the other the heavy chain of the immunoglobulin molecule. Upon expression of both chains in the cell according to the present invention these chains assemble to form the active antibody molecule. The expression cassettes of the two chains may be present on separated or on the same nucleic acid molecule. The coding sequences for the light and heavy chain may, however, be present within the same expression cassette and be separated by an IRES sequence (internal ribosome entry site) providing for an expression of both the heavy and the light chain. The coding sequences for the light and the heavy chain may in principle also be present within the same expression cassette and be separated by a sequence encoding an enzymatic cleavage site for a proteinase (e.g. thrombin) which is simultaneously expressed within the cell and which cleaves the precursor polypeptide consisting of the sequence of the light and heavy chain into the active light and heavy chain.

Recombinant antibodies encoded by the nucleic acid sequence of the cell according to the present invention may also consist of fragments of an antibody instead of the complete light and heavy chain. So called single chain antibodies (scFv, single chain variable fragments) consist of the variable domains of a heavy and a light chain linked by an amino acid sequence (a so called linker) providing for a free motility of both domains. An antigen binding structure is formed by the intramolecular assembly of both domains, which structure corresponds to the variable region of an immunoglobulin molecule. Bispecific single chain antibodies (bis-scFv) consist of two of such single chain assemblies made up of the variable domains of a heavy and a light chain which in turn are linked by a connecting sequence and are motile against each other; such molecules may simultaneously bind to two antigen binding sites (epitopes) thereby connecting two molecular structures in a non-covalent manner. Bispecific diabodies consist of two single chains which are expressed separately and each of which consist of variable domains of a light and a heavy chain each, separated only by a very short linker or they are without a linker at all. The short or lacking linker inhibits the intra molecular assembly; by intramolecular assembly of a variable heavy and light domain an active molecule having two binding valences is formed once more.

The recombinant polypeptide encoded by the nucleic acid molecule transfected in the present method may be a viral, bacterial or parasitic protein which is to be produced for a use as prophylactic or therapeutic vaccines. Thereby, this protein may be both a structural polypeptide and a regulatory or enzymatically active polypeptide from viruses, bacteria or parasites. A viral proteins may be, e.g., the hepatitis B virus surface antigen (HBV surface antigen) or the structural protein L1 from human papillomaviruses. A bacterial protein which is considered for the production of vaccines after the expression in production cell lines is, e.g., enterotoxine subunits from enterotoxinogeneous *Escherichia coli* (ETEC) or transferrin binding proteins (Tbp A and B) from *Neisseria gonorrhoeae*. A polypeptide from parasites, which polypeptide may be encoded by the nucleic acid molecules transfected in the present method is, e.g., the merozoite surface protein (MSP) of the causative agent of malaria *Plasmodium falciparum* or glutathione S transferase (GST) from *Schistosoma japonicum*.

The recombinant polypeptide encoded by the nucleic acid molecule transfected in the present method can also be a viral protein allowing a production of recombinant viral gene transfer vectors within the cell lines. This viral protein, also called complementation factor, is expressed within the cell line and is the enzymatic or structural component necessary for the production of the gene transfer vectors, which component is not encoded on the nucleic acid molecule of the gene transfer vector. In such gene transfer vectors certain viral gene functions are usually deleted because of security considerations. Gene transfer vectors, whose complementation factors may be encoded by the transgene introduced by the described method, are for example vectors which are based on adenovirus, adenovirus associated virus (AAV), retrovirus or lentivirus or herpes virus. The complementation factor expressed within the cell line may also complement deleted or recombinant viruses during their production, which viruses do not contain a gene to be transferred and thereby not acting as a gene transfer vector but are used, e.g., as a vaccine.

The polypeptide being transiently expressed by the present method can also be a receptor polypeptide which is in particular localized on the surface of the cell and which is responsible for the infection of the cell by a virus and the transduction of the cell by a viral gene transfer vector, respectively. As a viral receptor for the initial step of infection of cells with the adenovirus serotype 2 or 5, from which the most conventional adenoviral vectors are derived, the so called Coxsackie and adenovirus receptor, CAR, was identified (Bergelson et al., Science 275:1320-1323, 1997). The sufficient expression of CAR on the surface is a prerequisite that a cell is suitable to be a production cell for adenoviral gene transfer vectors. In a preferred embodiment the recombinant polypeptide is the Coxsackie and adenovirus receptor (CAR). The overexpression of the receptor polypeptide can significantly improve the infectibility and, thus, the production efficiency of these cells in regard to adenoviral vectors. Furthermore, the nucleic acid molecule may encode, besides CAR, secondary receptors or internalising receptors such as certain integrins that mediate the uptake of the virus and gene transfer vector, respectively, into the cell and whose additional expression is advantageous in the production of production cells for adenoviral vectors.

The described method may be used, inter alia, for the production of therapeutic polypeptides, blood clotting and growth factors, hormones and antibodies as well as viral, bacterial or parasitic polypeptides for use as vaccine. Moreover, the cells according to the present invention may be used for the production of diagnostically relevant proteins such as viral, bacterial or parasitic antigens or respective specific antibodies. Furthermore, the cells according to the present invention may be used for the production of technically or industrially relevant proteins such as enzymes for the catalysis of technical synthesis processes or for the degradation of harmful substances. The cells according to the present invention may express one or also more different recombinant polypeptides. The number of expressible polypeptides is dependent on how many different nucleic acid sequences encoding the recombinant polypeptides are transfected transiently into the cells with the method according to the present invention.

Further, the present invention relates to the use of permanent human cell lines, in particular permanent human amniocytic cell lines, produced by the method according to the present invention for the production of a polypeptide or protein.

The following examples illustrate the invention and are not to be considered limiting. Unless indicated differently, molecular standard methods were used such as described, e.g., by Sambrook et al., 1989, Molecular cloning: A Laboratory Manual, 2. Edition, Cold Spring Harbor Laboratory Press, Cold Spring Harbor, N.Y.

1. Cloning Procedures a. Plasmids for Transformation of Primary Amniocytes: pSTK146, pGS119, pGS122

Plasmid pSTK146 was described in detail in EP 1 230 354 B1 and comprises the murine phosphoglycerate kinase (pgk) promoter, adenovirus serotype 5 (Ad5) sequences nucleotide (nt.) 505 to 3522 and the splicing and polyadenylation signal of SV40. The adenoviral sequences in pSTK146 comprise the region encoding E1A and E1B, wherein the expression of E1A is regulated by the pgk promoter.

Plasmid pGS119 was described in detail in WO 2007/056994 and contains the murine pgk promoter, Ad5 sequences nt. 505-3522 (comprising the E1A and E1B region), the splicing and polyadenylation signal of SV40 followed by the pIX region of Ad5 nt. 3485-4079.

Plasmid pGS122 was described in detail in WO 2007/056994 and contains the adenoviral sequences nt. 1-4344 comprising the E1A, E1B and pIX regions including the respective regulatory promoter and polyadenylation sequences. The adenoviral sequences in pGS122 are flanked by PmeI restriction sites.

b. Expression Plasmids for T-antigen: pGS158, pGS159, pGS161

Plasmids pGS158, pGS159 and pGS161 all contain the expression cassette for T-antigen of SV40 (SEQ ID NO:4) flanked by an intron of SV40 (SEQ ID NO:6) and a polyadenylation site (SEQ ID NO:7). Additionally, pGS158 contains the CAG promoter (hybrid promoter consisting of a CMV enhancer and the chicken β-actin promoter) (Niwa et al., Gene 108:193-199, 1991), pGS159 contains the RSV promoter (promoter of Rous sarcoma virus) (GenBank acc. no. DQ075935) and pGS161 the CMV promoter (earlier promoter of human cytomegalovirus) (SEQ ID NO:5). For generation of stabile cell lines plasmids pGS158, pGS159 and pGS161 contain a blasticidin expression cassette with the ubiquitin promoter (pUB/Bsd, Invitrogen #V512-20).

In a first step a 2.6 kb fragment containing the sequence encoding the T-antigen was introduced into the plasmid pGS140. The plasmid pGS140 contains the human CMV-promoter (SEQ ID NO:5), an intron region of SV40 with splicing donor/splicing acceptor site (SEQ ID NO:6), a singular NotI restriction site and a PolyA sequence of SV40 (SEQ ID NO:7). For introducing the T-antigen fragment pGS140 was linearized with NotI, the 5' overhang was filled up and ligated with the isolated fragment. The plasmid produced by this procedure was named pGS149.

For plasmid pGS158 the pGS149 was digested with XbaI and an about 3-kb fragment containing the intron sequence, the T-antigen and the PolyA sequence was isolated. This fragment was introduced into the NotI restriction site (5' overhang filled up) of pGS152. pGS152 was produced by insertion of a CAG promoter fragment having a size of 1.1 kb (Niwa et al., Gene 108:193-199, 1991) into the EcoRV restriction site of pUB/Bsd.

For plasmid pGS159 a XbaI fragment having a size of 3 kb and containing the T-antigen of pGS149 was introduced into the filled up NotI restriction site of pGS153. pGS153 contains a RSV promoter fragment having a size of about 0.6 kb introduced into the EcoRV restriction site of pUB/Bsd.

For plasmid pGS161 the pGS149 was digested with SphI, the 3' overhangs were filled up and the 3.6 kb fragment containing the CMV promoter, the SV40 intron, the T-antigen sequence and the PolyA were isolated and introduced into the EcoRV restriction site of pUB/Bsd.

c. Expression Plasmids for hAAT: pGS116, pGS151

Plasmid pGS116 was described in detail in EP1948789 and contains the human CMV promoter followed by a SV40 splicing donor/splicing acceptor site, the hAAT-cDNA (SEQ ID NO:12) and the SV40 polyadenylation site.

Figure 2A:
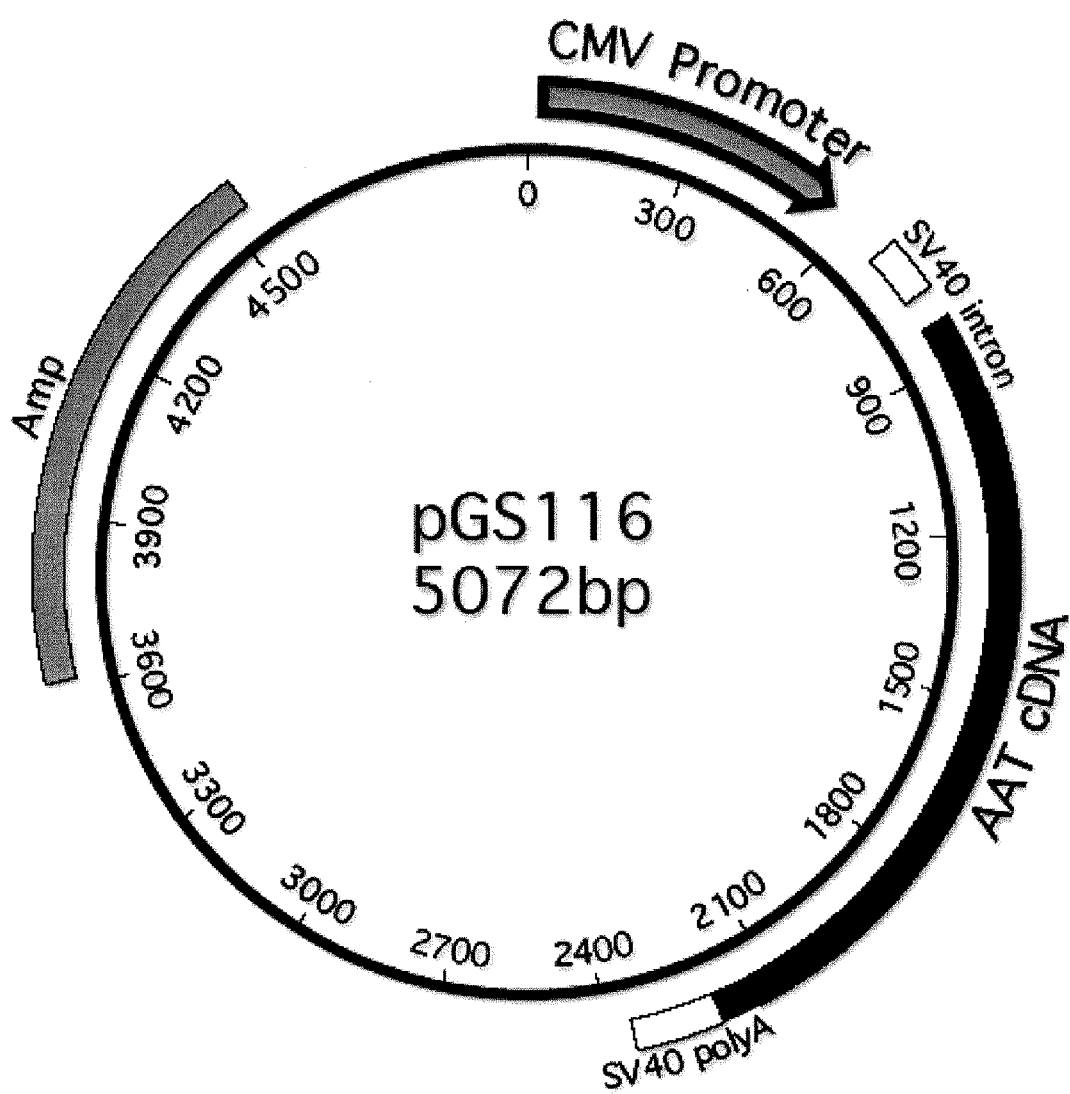
Figure 2B:
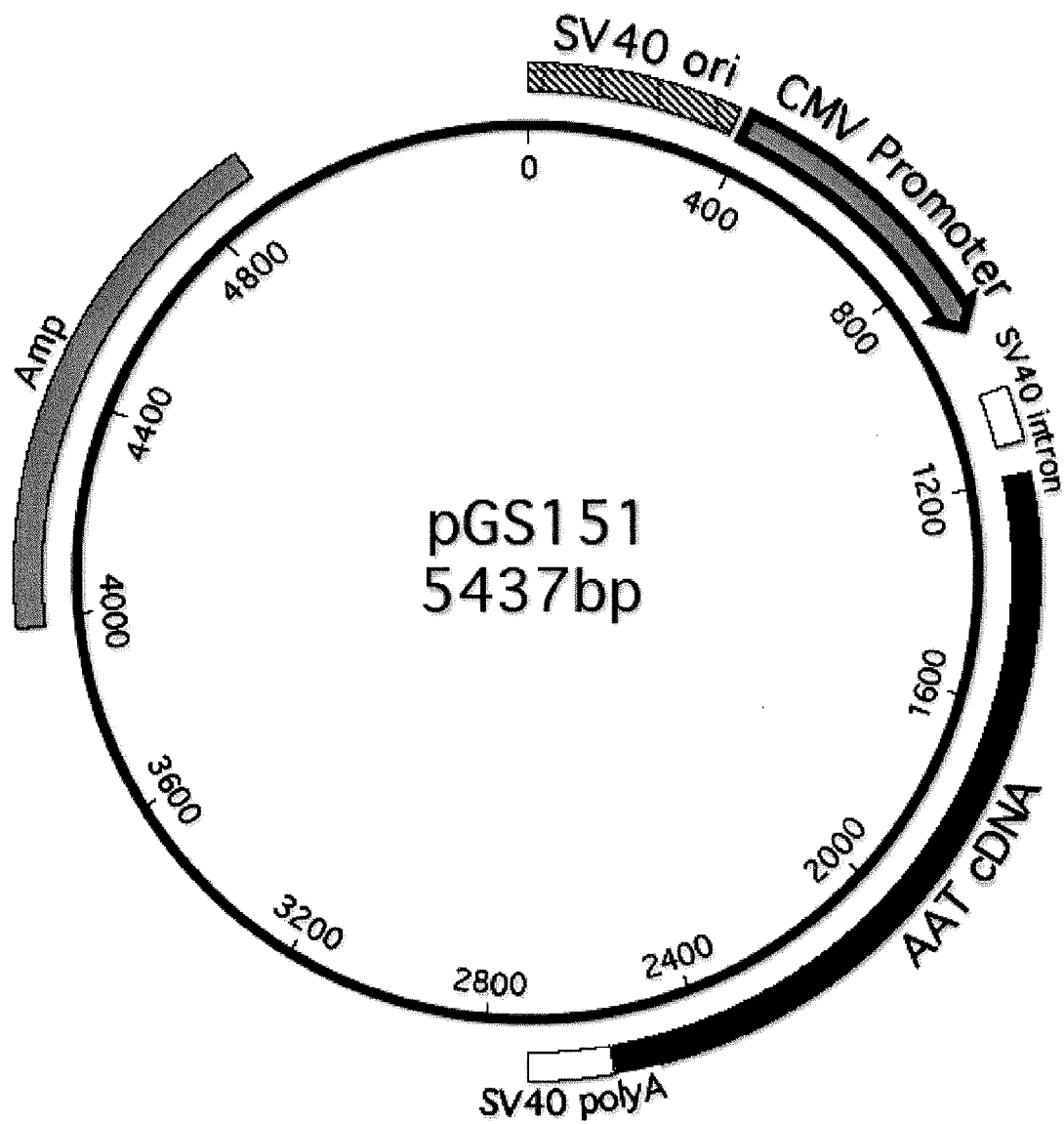
Figure 2C:
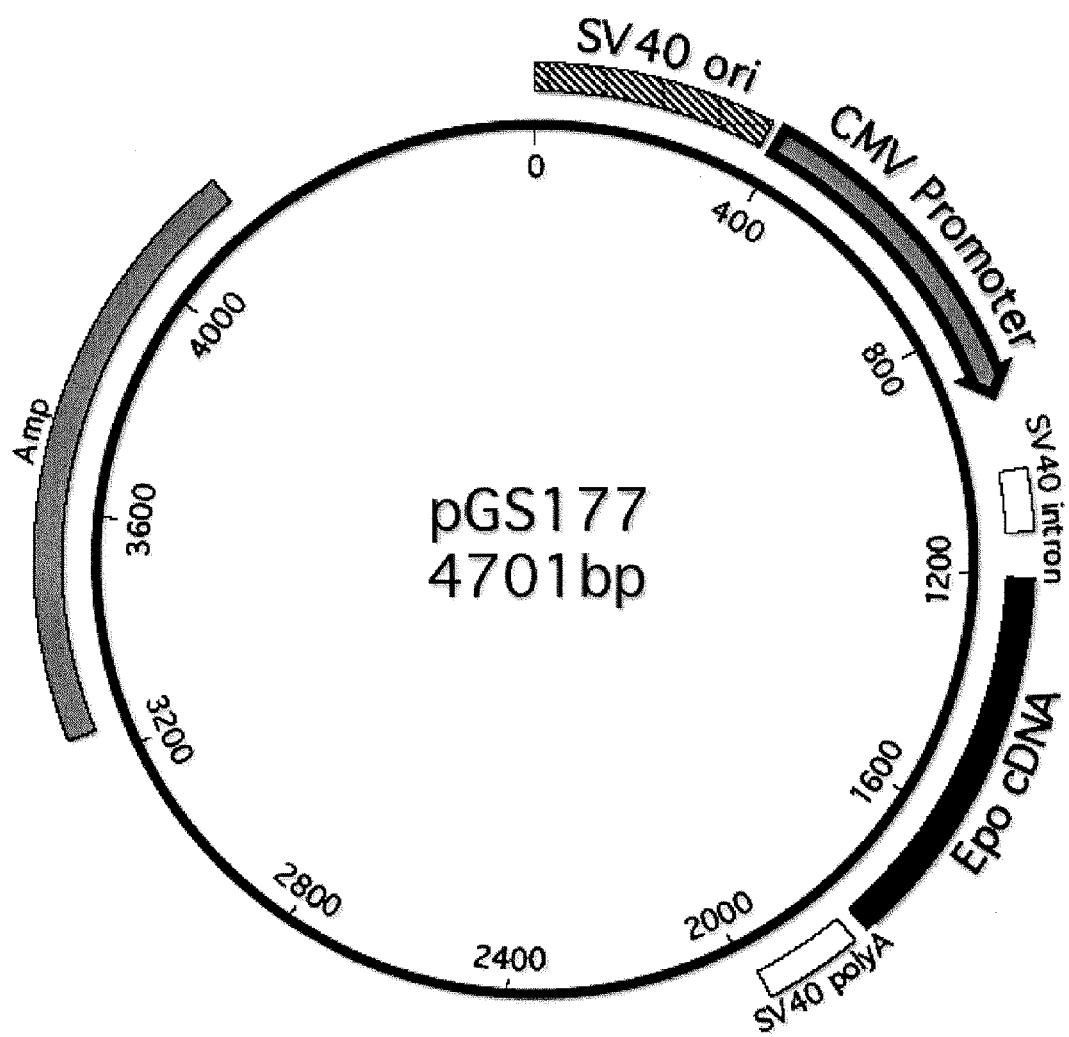

Plasmid pGS151 (FIG. 2b) contains said hAAT expression cassette and the origin of DNA replication (ori) of SV40. By means of the SV40 DNA and the primer on 1 (CCGGAATTCTTTGCAAAAGCCTAGGCCTC) (SEQ ID NO:9) and on 2 (CCGGAATTCTGAGGCGGAAAGAACCAGCT) (SEQ ID NO:10) the SV40 sequences were amplified by polymerase chain reaction (PCR), digested with EcoRI (each one EcoRI restriction site is located in the primers) and introduced into the EcoRI restriction site of pGS116.

d. Expression Plasmids for Epo: pGS177

Plasmid pGS127 was described in detail in EP1948789 and contains the human CMV promoter followed by a SV40 splicing donor/splicing acceptor site, the cDNA for human erythropoietin (Epo) and the SV40 polyadenylation site.

For plasmid pGS177 the on fragment of SV40 was amplified as described above with the primers on 1 and on 2 and introduced into pGS127.

2. Verification of the Constructs a. Sequence Analysis

The completeness of all plasmids described above was tested by restriction digest. Furthermore, the correct sequence and orientation of the SV40 on fragments in pGS151 and pGS177 was confirmed by sequence analysis. The adenoviral sequences in pSTK146, pGS119 and pGS122 were determined by sequence analysis and matched completely with the Ad5 wild type sequence.

b. Testing for the Transient Expression

The plasmids pSTK146, pGS119 and pGS122 were transfected into HeLa cells and the expression of the E1A and E1B proteins was analyzed via Western blotting by using monoclonal antibodies (Merck Bioscience). The plasmids pGS158, pGS159, pGS161 were transfected into HEK293 cells and the expression of the T-antigen was detected using Western blotting and a monoclonal antibody (Abcam, Cambridge, UK). The plasmids pGS116 and pGS151 were transfected into CAP cells and the expression and secretion of human alpha 1-antitrypsin (hAAT) into the culture supernatant was detected using ELISA (see 6.).

In the same way plasmids pGS127 and pGS177 were transfected in CAP cells and the expression of human Epo was detected using ELISA (see 6.).

3. Cultivation of Cells a) Cell Lines

Transformed amniocytes (CAP and CAP-T) cells were cultivated in 293SFMII medium (Invitrogen #11686-029), 0.5% antimycotic/antibiotic (Invitrogen #15240-062), 4 mM L-glutamine (Invitrogen #25030-024) at 37° C., 95% humidity, 8% $CO_2$. The culture medium of CAP-T cells additionally contained 5 µg/ml blasticidin (Invitrogen # R210-01). The cells were usually inoculated with a starting density of 2-4×$10^5$ cells/ml in a volume of 12 ml in a shaking flask and cultured in the shaking incubator at 100 rpm for 3-4 days. At a density of 1-2×$10^6$ cells/ml cells were harvested by centrifugation and further cultivated with the above mentioned starting density in fresh medium. HEK293, HEK293-T (ATCC#CRL-11268) and HeLa cells were cultivated adherently in Dulbecco's modified Eagle's medium (Advanced D-MEM, Invitrogen #12491-015) with 10% fetal calf serum in cell culture dishes. HEK293-T cells were stepwise adapted to serum free suspension growth in 293-SFMII medium and cultivated in shaking flasks at 100 rpm, 37° C., 95% humidity and 8% $CO_2$.

b. Primary Amniocytes

Primary amniocytes were, following respective routine methods, obtained during an amniocentesis. 1-2 ml of this puncture were cultivated with 5 ml Ham's F10 medium (Invitrogen #31550-023), 10% fetal calf serum, 2% Ultroser G (CytoGen GmbH), 1× antibiotic/antimycotic (Invitrogen #15240-062) at 37° C., 95% humidity and 5% $CO_2$ in 6 cm Primaria cell culture dishes (Falcon). After 4-6 days the amniocytes started to become adherently and 3 ml fresh medium plus additives (see preceding set) were added. As soon as the cells were fully adherently, the medium was removed and replaced by 5 ml fresh medium plus additives. For the further passages the confluent cells were washed with PBS, detached with trypsin (TrypleSelect, Invitrogen #12563011) and transferred into 10 and 25 ml, respectively, fresh medium plus additives into 10 cm and 15 cm dishes, respectively.

4. Transformation of Primary Amniocytes a. Transfection

The cultivated primary amniocytes (see 3b) were each transformed by the transfection with plasmids pSTK146, pGS119 or pGS122. In advance, the respective plaspmids were linearized by a digest with suitable restriction enzymes (pSTK146, pGS119: ScaI; pGS122: PmeI). Prior to the transfection the amniocytes were stepwise adapted to Opti-Pro medium (Invitrogen #12309-019) with 2% Ultroser. For this purpose, the cells were each spiked with fresh Ham's F10 medium (with additives see 3b) plus Opti-Pro medium (with 2% Ultroser) in a ratio of 75:25%, 50:50%, 25:75% and 0:100% every 2-3 days. For the transfection, the cells of an approximately 80% confluent 15 cm dish were distributed onto 6 cm dishes corresponding to a cell number of 5-7×$10^5$ cells per dish. On the following day, the cells on 5 dishes were transfected with each 2 µg linearized pSTK146, pGS119 or pGS122 using the transfection reagent Effectene (Qiagen) according to the manufacturer's protocol. One dish was not transfected and further cultivated. On the next day, the cells were washed with PBS, detached with TrypleSelect and transferred to a 15 cm dish. The cells were cultivated for further 10-15 days, wherein the medium was replaced by fresh medium every 3-4 days. During this time the addition of Ultroser was decreased to 1%. After about 10-15 days the cells were confluent and were transferred to 15 cm dishes, as described above.

b. Isolation of the Transformed Cell Clones

A few weeks after the transfection, clonal cell islands being significantly distinct from the non-transformed amniocytes in regard to their morphology were observed in all transfections. These cell islands were picked and transferred onto 24-well-dishes (corresponding to passage 1). Furthermore, the cells were propagated and firstly transferred to 6 cm dishes and later to 15 cm dishes. The expression of the E1 proteins in each of the clonal cell lines were detected in Western blot analysis using monoclonal antibodies (see 2b).

The production of cell lines expressing T-antigen based on transformed amniocytic cell lines is described in the following exemplarily for a cell line obtained by transfection with pGS119 (said cell line is called CAP cell line in the following). After isolation and expansion of the clonal cell islands genetic uniform cell lines were produced from the cell clones by single cell cloning via the "limited-dilution method". Summarized a cell of the clone to be cloned were plated into a 96 well plate and the actual expansion of only one cell was controlled microscopically in the course of the following days. Lines obtained from single cells were stepwise expanded up to 15 cm dishes. By stepwise dilution of the culture medium Opti-Pro/1% Ultroser with 293SFMII medium cells were adapted to growth in suspension in serum free medium. The singe cell lines were analyzed for stable and transient protein expression and high growth density, a clone with the best properties was selected and continued to be used in the following.

5. Production of Cell Pools Expressing T-antigen

Each $1 \times 10^7$ CAP cells (obtained by transfection of primary amniocytes with plasmid pGS119, adapted to suspension growth in serum free medium) were transfected with each 5 µg linearized pGS158-, pGS159- and pGS161 plasmid DNA and cultured in the shaking flask under conditions as described above. For the selection of stable transfected cells 5 µg/ml blasticidin were added 48 h after transfection and the cells were cultured further until stable growing cell pools were obtained after about 3-4 weeks. Said cell pools were named Z582 (transfection with pGS158, T-antigen expressed by CAG promoter), Z583 (transfection with pGS159, T-antigen expressed by RSV promoter) and Z597 (transfection with pGS161, T-antigen expressed by CMV promoter). Since it is unknown whether an increased T-antigen concentration is potentially toxic for CAP cells it was tried to express T-antigen by means of promoters having different strengths. It was possible to show that the expression of a reference protein in CAP cells was highest by use of the CMV promoter, a little bit lower with the CAG promoter and clearly lower with the RSV promoter. It was possible to generate stable growing cell pools with all three promoters and all three cell pools expressed the intracellular T-antigen.

6. Transient Protein Expression in CAP and CAP-T Cells

The 359-bp ori-Fragment as used here contains in comparison to the minimal on being 63 bp in length in addition to said core sequence also the 21-bp and 72-bp repeating sequences (SEQ ID NO: 11). These two repeating sequences are indeed mainly important for the function of the promoter overlapping the on but there are hints that they also increase the replication of SV40 DNA (Chandrasekharappa and Subramanian, J. Virol. 61, 2973-2980, 1987).

For testing whether the concentration of T-antigen in the cell has an influence on the expression of a reference protein the three cell pools Z582, Z583 and Z597 expressing the T-antigen under promoters of different strengths have been tested and compared with the transient expression in CAP cells not expressing T-antigen. Therefore, each $1 \times 10^7$ cells were transfected with means of the nucleofector technology (Amaxa/Lonza, program X-001, Puffer V) with the circular plasmid pGS151 and cultured in a starting volume of 12 ml. The medium was replaced three and six days after transfection, wherein on day 6 also the volume was increased to 15 ml. Each one aliquot was taken beginning on the third day up to and including the seventh day after transfection and on the ninth day after transfection, the cell number was determined and the expression of hAAT was determined by the ELISA (enzyme-linked immunosorbent assay) method using polyclonal anti-hAAT antibodies (uncoupled and coupled to HRP; ICN Biomedicals). hAAT purified from human plasma (ICN Biomedicals) was used as control.

Figure 3:
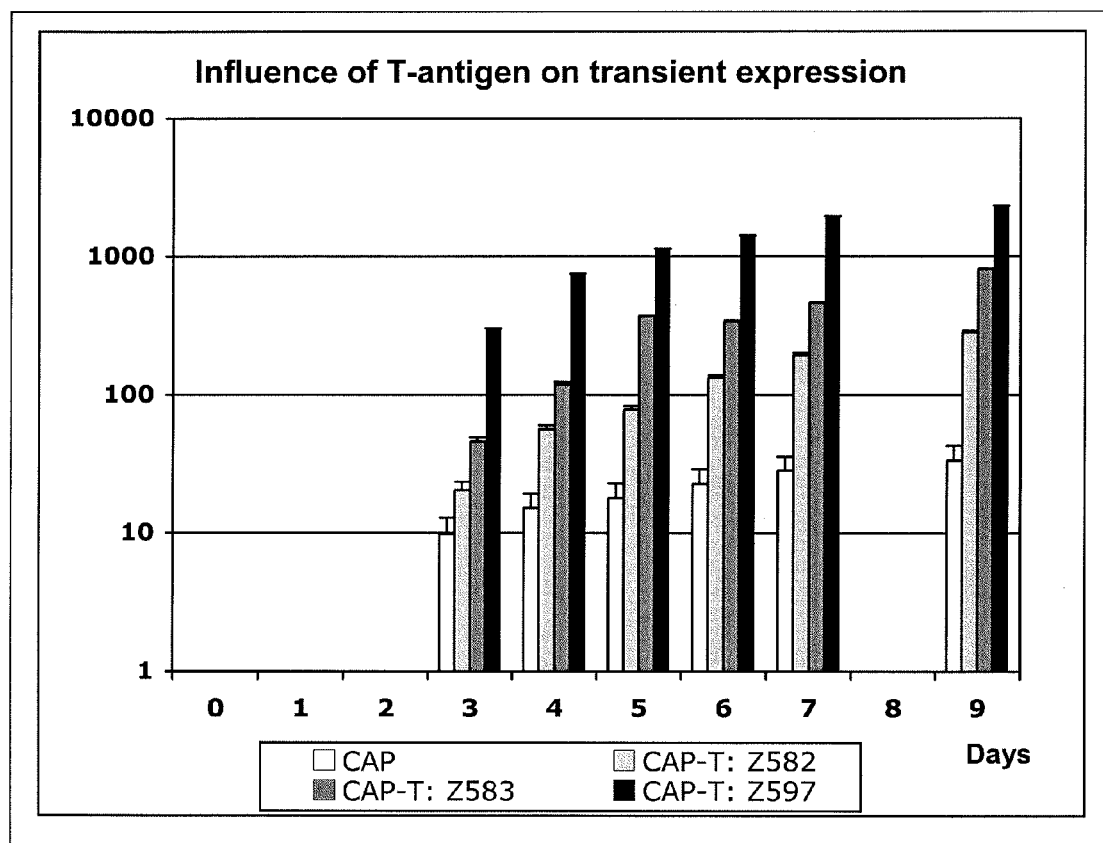

The result of this experiment is graphically shown in FIG. 3. In all cell pools of CAP-T a higher transient expression was obtained in comparison to the CAP cells. The transient expression in Z582 is 8 times, in Z583 it is 25 times and in Z597 it is 70 times higher than in CAP cells. Also a second CAP-T cell pool expressing T-antigen by the CMV promoter results in a comparable high expression as expression obtained with Z597.

Said data demonstrate that both the permanent expression of T-antigen in CAP cells and the level of T-antigen expression have an influence on the level of transient expression.

Figure 4:
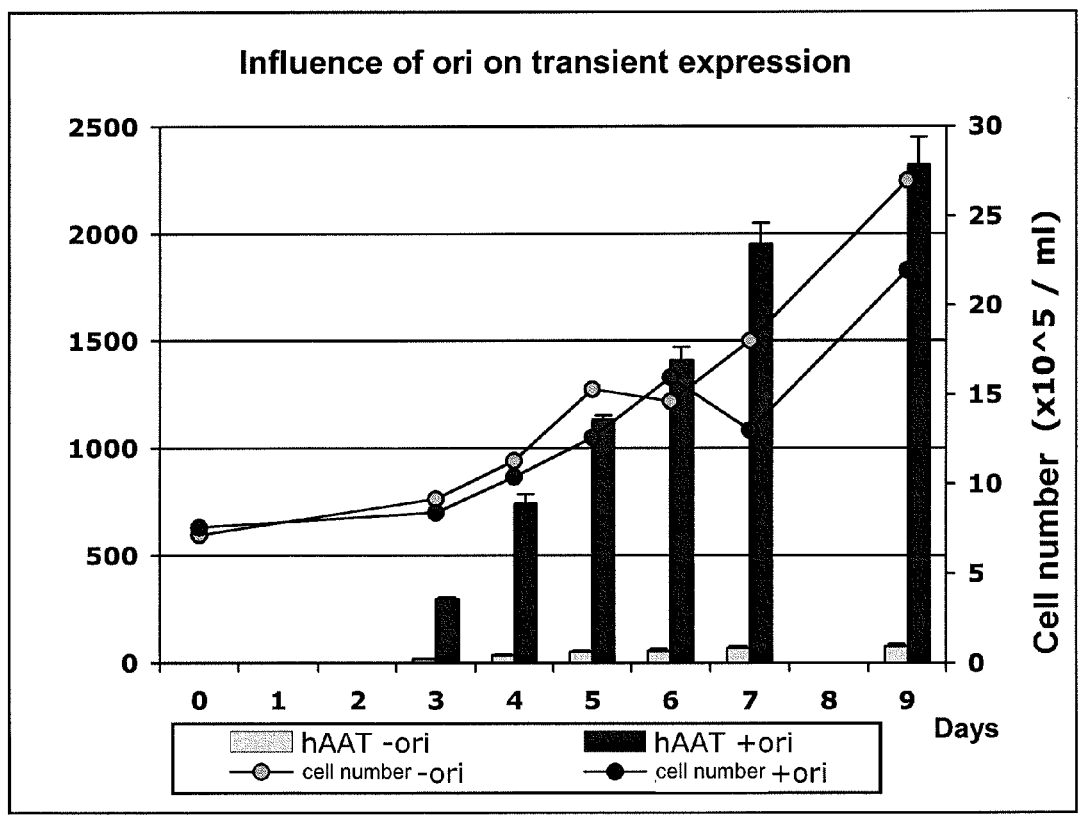
FIG. 4 shows schematically the amount of transiently expressed hAAT (bars) in the culture supernatant and the cell number of living cells (lines) at different time points after the transfection of a plasmid without SV40 on (hAAT/cell number−ori, plasmid pGS116) and with SV40 ori (hAAT/cell number+ori, pGS151), respectively.

In a further experiment the level of transient expression of hAAT was determined in the cell pool Z597 after transient transfection of the plasmid pGS116 and pGS151, respectively. Both of said plasmids differ from each other only in the presence of the SV40-ori fragment in pGS151. The transfection and quantitative analysis of hAAT was performed as described above, wherein both the level of expression of hAAT and the development of the cell number of living cells was determined over a time range of 9 days. The result of said test is graphically shown in FIG. 4. The presence of the SV40-ori fragment in the expression plasmid leads to an increased transient expression being 30 times higher. In total 2.5 mg hAAT could be expressed by transfection of $1 \times 10^7$ CAP-T cells in 40 ml volume within 9 days. This corresponds with an expression efficiency of about 60 mg/L and up to 40 pg/cell/day. The cell growth starts about 3 days after transfection, the vitality of the cells further remains over the whole time range of the test above 80%.

For demonstrating that said transient expression efficiency is not specific for hAAT a further high glycosylated protein erythropoietin (Epo) was expressed transiently in CAP-T cells. As described for hAAT $1 \times 10^7$ CAP-T cells of the Z597 cell pool were transfected with plasmids pGS177 (containing the expression cassette for Epo and the SV40-ori fragment) and Epo was quantified in the cell supernatant via ELISA (R&D Systems, Quantikine IVD, Human Epo Immunoassay, DEP00). 0.73 mg Epo could be expressed at an expression efficiency of 32 mg/L in a test time range of 7 days.

7. Comparison with Transient Expression in Other Cell Systems

Figure 5:
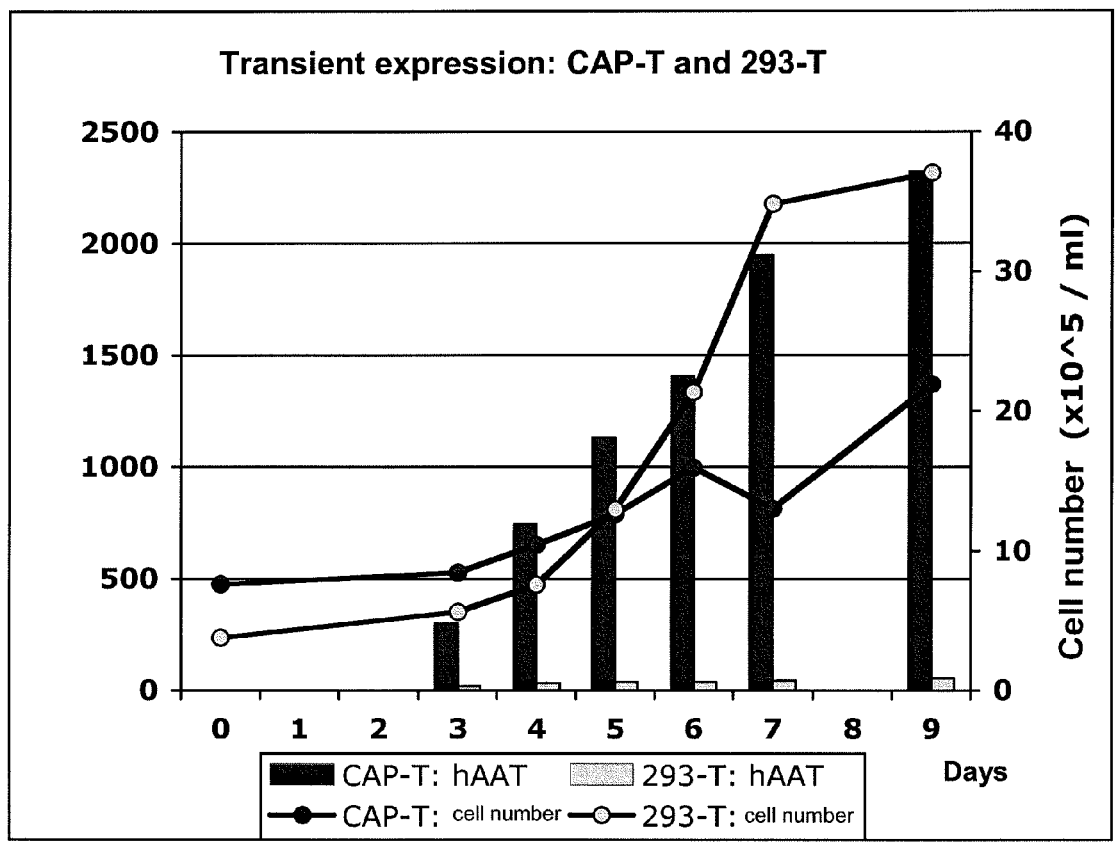
FIG. 5 shows schematically the amount of transiently expressed hAAT (bars) in the culture supernatant and the cell number of living cells (lines) at different time points after the transfection of pGS151 (with SV40 ori) in CAP-T and HEK293T cells.

An already previously described human cell line, the so called HEK293-T cell line, expresses the SV40 T-antigen stably and is based on the human HEK293 cell line transformed with adenovirus (DuBridge et al., Mol. Cell. Biol. 7, 379-387, 1987). Comparable with Z597 $1 \times 10^7$ HEK293-T cells (serum free medium, suspension culture) were transfected with 5 µg circular plasmid pGS151 by means of the Amaxa nucleofektor technology according the manufacture's protocol (program X-001, Puffer V) and cultured. The result of said experiment is shown graphically in FIG. 5. Although the cell number of 293-T was clearly higher than that one of CAP-T on day 9 the transient expression in CAP-T is in comparison to that one in 293-T about 40 times higher.

8. Replication Assay

Figure 6:
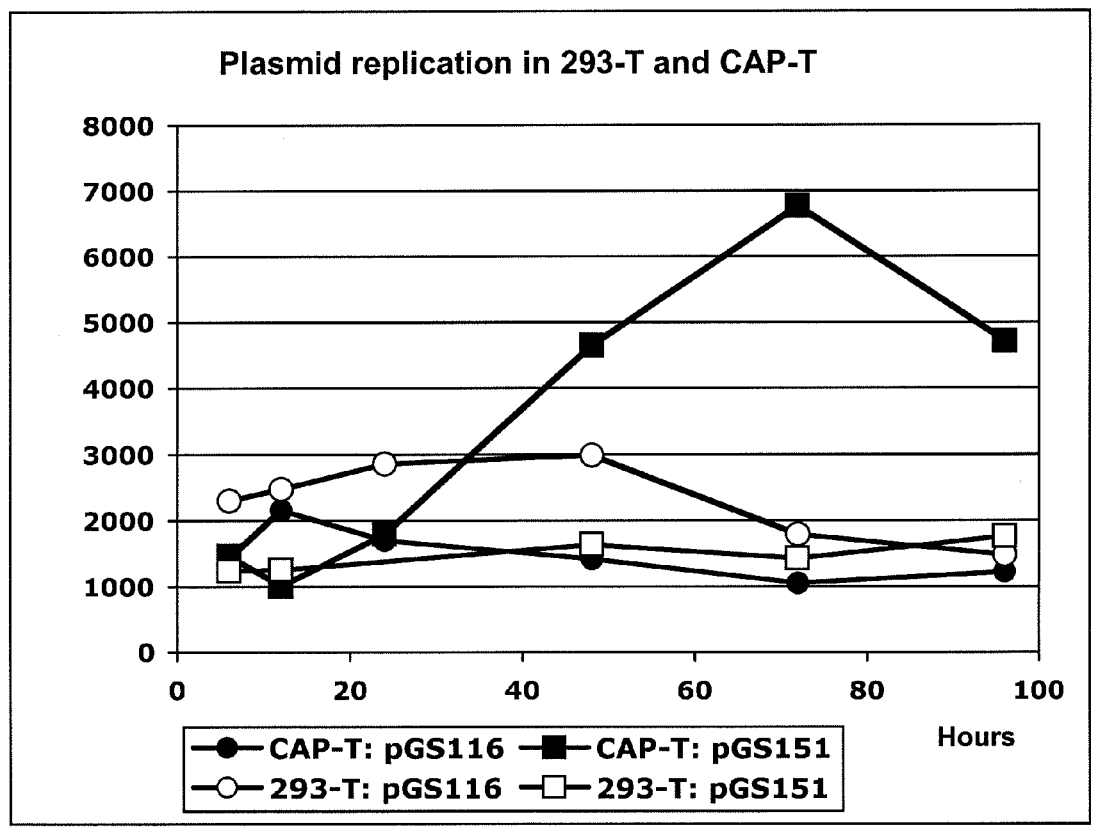
FIG. 6 shows schematically the intracellular copy number of plasmids pGS116 (without SV40 ori) and pGS151 (with SV40 ori), respectively, at different time points after the transfection in CAP-T and HEK293-T cells.

It should be shown in a replication assay, whether the expression of T-antigen in CAP-T cells results in a higher copy number of the on containing expression plasmid—that would thus explain the transient protein expression to be clearly higher. Therefore, Z597- and HEK293-T cells, respectively, were transfected with the plasmids pGS116 and pGS151, respectively, and cultured as described above. After 6, 12, 24, 48, 72 and 96 hours each $1 \times 10^5$ cells were taken, centrifuged, taken up in PBS and lysed by the addition of the same volume of 0.8 N NaOH. The cell lysates were blotted in a SlotBlot apparatus on a positive charged nylon membrane (GE Healthcare, Hybond–N+). Increasing amounts of plasmids pGS116 and pGS151 were added to $1 \times 10^5$ Z597 cells as control, lysed and blotted as described above. Said standard corresponds to 1000, 2500, 5000, 10000 and 15000 copies per cell. The DNA was fixed by incubating the membrane at 120° C. for 30 minutes and visualized by means of a non radioactive PCR probe composed of hAAT-cDNA according to the manufacture's protocol (AlkPhos Direct Labeling and Detection System, GE Healthcare, RPN 3680 and 3682). The number of copies in cells transfected with pGS116 and pGS151 was quantified by means of the known concentration of the standard plasmid. The result of said replication assay is graphically shown in FIG. 6. As expected only pGS151 but no pGS116 is replicated in CAP-T Z597. The number of copies of pGS151 increases from about 1500 copies/cell 6 h after transfection to almost 7000 copies/cell 72 h after transfection, whereby the cell number remains the same. In contrast thereto, the number of copies of pGS151 remains constant in HEK293-T for over 96 h. Since the cell number of 293-T cells has been doubled in said time span a low replication of pGS151 can be assumed in said cells, however, it is clearly beneath the replication rate of Z597.

The detection of the expression of the T-antigen in amniocytic cell lines and HEK293-T cells was performed by Western blot analysis. From the three CAP-T cell pools and HEK293-T cells each $1 \times 10^6$ cells were taken up in 50 µl 50 mM Tris/HCL pH 8, 140 mM NaCl, 0.5% NP40, 4 mM EDTA, 2 mM EGTA, 0.5 mM PMSF, 5% glycerol and incubated for 30 min on ice. The protein mixture was centrifuged for 10 min at 13 000 rpm and the protein concentration was determined in the supernatant by means of a protein detection kit (Coomassie, Bradford, Thermo Life Science# 23200). On a 12% SDS polyacrylamide gel each 10 µg protein were separated, transferred onto a nitrocellulose membrane (Hybond ECL, Amersham Pharmacia Biotech) and visualized by means of a T-antigen specific antibody (Abcam, Anti-SV40 T-Antigen ab16879). It could be shown by this experiment that more T-antigen is expressed in Z597 than in the other two pools and in HEK-293-T cells.

9. Transfection with Polyethylenimine

Figure 7:
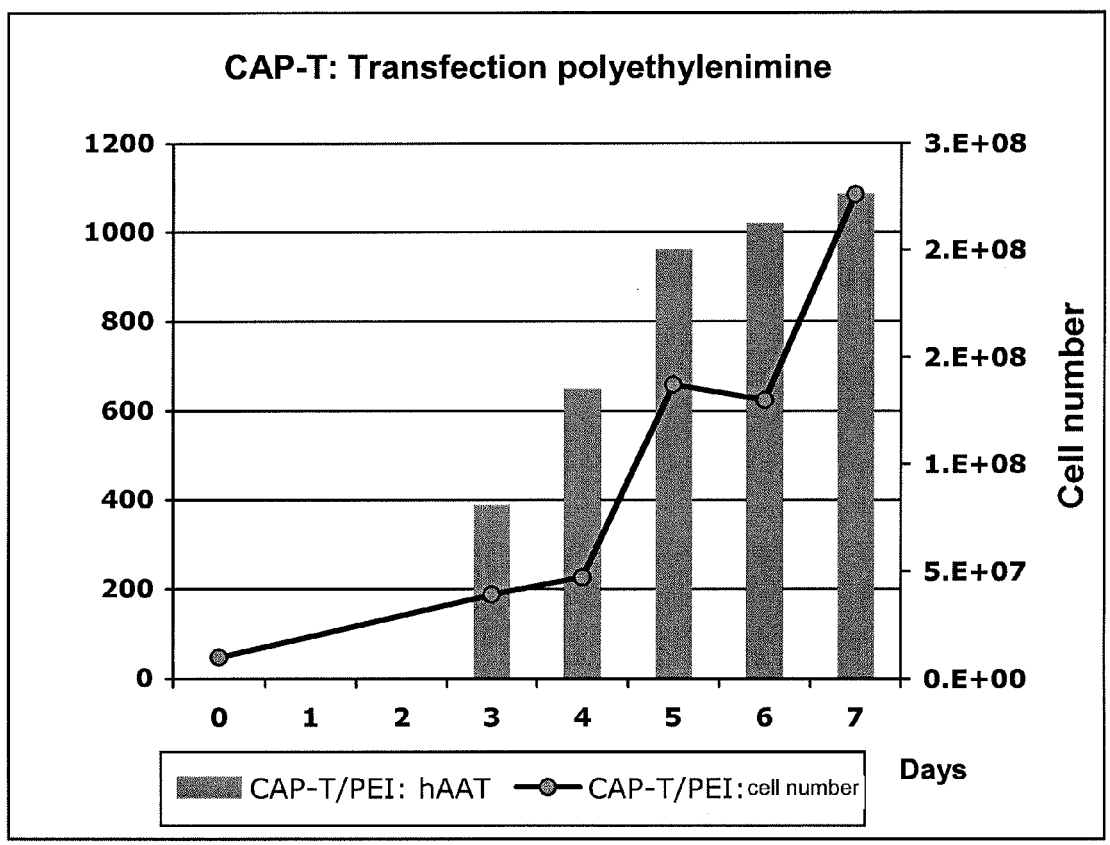
FIG. 7 shows schematically the amount of transiently expressed hAAT (bars) in the culture supernatant and the cell number of living cells (lines) at different time points after the transfection of pGS151 (with SV40 ori) in CAP-T with polyethylenimine (PEI) as transfection reagent.

Since the transfection method described above is only scalable in a limited way, a further transfection reagent, polyethylenimine (PEI, Polysciences, #23966) being described in particular for transfections in large scale, has been tested. Linear PEI (MW=25,000) were dissolved according to the manufacture's protocol with a concentration of 1 mg/ml and used in a ration of DNA:PEI=1:3. For the transfection 10 µg pGS151 were mixed with 30 µg PEI, incubated for 10 min at room temperature and added to $1 \times 10^7$ CAP-T Z597 cells in 6 ml FreeStyle medium (Invitrogen #12338-018). 6 ml of 293-SFMII medium were added after 5 h and the cells were incubated for 7 days. Three days after transfection the medium was replaced by 293-SFMII and in view of the strong cell growth the volume was increased up to 30 ml. The result of said experiment is shown in FIG. 7. By the transfection with PEI a high transient expression of proteins was achieved in CAP-T. However, the maximum yield of protein was about 2 times beneath of that expression achieved with nukleofection. It is remarkable that the cells grow clearly faster and stronger after transfection with PEI and achieve a cell number being about 10 times higher in comparison to nucleofection after 7 days.

The invention claimed is:

1. A method for the production of a permanent human amniocytic cell line comprising:
   a) transfecting primary human amniocytic cells with a nucleic acid molecule comprising a nucleic acid sequence encoding the human adenoviral serotype 5 gene products E1A and E1B to produce clonal transformed human amniocytic cells;
   b) isolating and expanding the clonal cells to produce a single transformed human amniocytic cell clone;
   c) expanding the single transformed human amniocytic cell clone of step (b) to produce a uniform transformed human amniocytic cell line having stable, high growth density and transient protein expression, and
   d) stably transfecting the transformed human amniocytic cells of step (c) with a nucleic acid molecule comprising a nucleic acid sequence encoding the SV40 large T-antigen operably linked to a CMV promoter or CAG promoter to produce a permanent human amniocytic cell line expressing SV40 large T-antigen,
   wherein said permanent human amniocytic cell line exhibits about a 25 to 70 fold increase in transient expression of recombinant protein compared to amniocytic cells not expressing SV40 large T-antigen when subsequently transfected with a nucleic acid encoding the recombinant protein.

2. The method of claim 1, wherein the human adenovirus serotype 5 sequence comprises the nucleotides 1 to 4344, 505 to 3522 or the nucleotides 505 to 4079 of the human adenovirus serotype 5.

3. The method of claim 1, wherein the nucleic acid sequence encoding the SV40 large T-antigen further comprises a nucleic acid sequence for SV40 SD/SA (intron) and the nucleic acid sequence for SV40 polyA.

4. A method for transient expression of a recombinant polypeptide from the permanent human amniocytic cell line of claim 1 comprising:
   a) transfecting the permanent human amniocytic cell line expressing SV40 large T-antigen with a nucleic acid molecule comprising a nucleic acid sequence encoding a recombinant polypeptide and a recognition or binding site for SV40 large T-antigen therein,
   b) culturing the permanent human amniocytic cell line under conditions allowing the expression of said recombinant polypeptide, and subsequently
   c) isolating said recombinant polypeptide from the cells or from the culture supernatant.

5. The method of claim 4, wherein the recombinant polypeptide is a hormone, a plasma factor, a blood clotting factor, a growth factor, a cellular receptor, a fusion protein, a Coxsackie and adenovirus receptor (CAR), an antibody, a viral, bacterial or parasitic antigen or complement factor for the production of recombinant viruses.

6. The method of claim 1, wherein said permanent human amniocytic cell line exhibits about a 30-fold increase in transient expression of recombinant protein compared to amniocytic cells not expressing SV40 large T-antigen.

7. The method of claim 1, wherein said permanent human amniocytic cell line exhibits about a 40-fold increase in transient expression of recombinant protein compared to amniocytic cells not expressing SV40 large T-antigen.

8. The method of claim 1, wherein said permanent human amniocytic cell line exhibits about a 70-fold increase in transient expression of recombinant protein compared to amniocytic cells not expressing SV40 large T-antigen.

* * * * *

SEQUENCE LISTING

<160> NUMBER OF SEQ ID NOS: 12

<210> SEQ ID NO 1
<211> LENGTH: 4344
<212> TYPE: DNA
<213> ORGANISM: Artificial
<220> FEATURE:
<223> OTHER INFORMATION: Synthetic primer
<220> FEATURE:
<223> OTHER INFORMATION: 1-4344 Ad5

<400> SEQUENCE: 1

| | | | | | | |
|---|---|---|---|---|---|---|
| catcatcaat | aatatacctt | attttggatt | gaagccaata | tgataatgag | ggggtggagt | 60 |
| ttgtgacgtg | gcgcggggcg | tgggaacggg | gcgggtgacg | tagtagtgtg | gcggaagtgt | 120 |
| gatgttgcaa | gtgtggcgga | acacatgtaa | gcgacggatg | tggcaaaagt | gacgttttg | 180 |
| gtgtgcgccg | gtgtacacag | gaagtgacaa | ttttcgcgcg | gttttaggcg | gatgttgtag | 240 |
| taaatttggg | cgtaaccgag | taagatttgg | ccattttcgc | gggaaaactg | aataagagga | 300 |
| agtgaaatct | gaataatttt | gtgttactca | tagcgcgtaa | tatttgtcta | gggccgcggg | 360 |
| gactttgacc | gtttacgtgg | agactcgccc | aggtgttttt | ctcaggtgtt | ttccgcgttc | 420 |
| cgggtcaaag | ttggcgtttt | attattatag | tcagctgacg | tgtagtgtat | ttatacccgg | 480 |
| tgagttcctc | aagaggccac | tcttgagtgc | cagcgagtag | agttttctcc | tccgagccgc | 540 |
| tccgacaccg | ggactgaaaa | tgagacatat | tatctgccac | ggaggtgtta | ttaccgaaga | 600 |
| aatgccgcc | agtcttttgg | accagctgat | cgaagaggta | ctggctgata | atcttccacc | 660 |
| tcctagccat | tttgaaccac | ctaccctca | cgaactgtat | gatttagacg | tgacggcccc | 720 |

```
cgaagatccc aacgaggagg cggtttcgca gattttccc gactctgtaa tgttggcggt      780
gcaggaaggg attgacttac tcactttcc gccggcgccc ggttctccgg agccgcctca      840
cctttcccgg cagcccgagc agccggagca gagagccttg ggtccggttt ctatgccaaa    900
ccttgtaccg gaggtgatcg atcttacctg ccacgaggct ggcttccac ccagtgacga     960 cgaggatgaa gagggtgagg agtttgtgtt agattatgtg gagcaccccg ggcacggttg   1020
caggtcttgt cattatcacc ggaggaatac gggggaccca gatattatgt gttcgctttg   1080
ctatatgagg acctgtggca tgtttgtcta cagtaagtga aaattatggg cagtgggtga   1140
tagagtggtg ggtttggtgt ggtaatttt ttttaattt ttacagtttt gtggtttaaa    1200
gaattttgta ttgtgatttt tttaaaaggt cctgtgtctg aacctgagcc tgagcccgag   1260
ccagaaccgg agcctgcaag acctaccgc cgtcctaaaa tggcgcctgc tatcctgaga   1320
cgcccgacat cacctgtgtc tagagaatgc aatagtagta cggatagctg tgactccggt   1380
ccttctaaca cacctcctga gatacacccg gtggtcccgc tgtgcccat taaaccagtt   1440 gccgtgagag ttggtgggcg tcgccaggct gtggaatgta tcgaggactt gcttaacgag   1500
cctgggcaac cttttggactt gagctgtaaa cgccccaggc cataaggtgt aaacctgtga   1560
ttgcgtgtgt ggttaacgcc tttgtttgct gaatgagttg atgtaagttt aataaagggt   1620
gagataatgt ttaacttgca tggcgtgtta aatggggcgg ggcttaaagg gtatataatg   1680
cgccgtgggc taatcttggt tacatctgac ctcatggagg cttgggagtg tttggaagat   1740
ttttctgctg tgcgtaactt gctggaacag agctctaaca gtacctcttg gttttggagg   1800
tttctgtggg gctcatccca ggcaaagtta gtctgcagaa ttaaggagga ttacaagtgg   1860
gaatttgaag agcttttgaa atcctgtggt gagctgtttg attctttgaa tctgggtcac   1920
caggcgcttt tccaagagaa ggtcatcaag actttggatt tttccacacc ggggcgcgct   1980
gcggctgctg ttgctttttt gagttttata aaggataaat ggagcgaaga aacccatctg   2040 agcgggggt acctgctgga ttttctggcc atgcatctgt ggagagcggt tgtgagacac    2100
aagaatcgcc tgctactgtt gtcttccgtc cgcccggcga taataccgac ggaggagcag   2160
cagcagcagc aggaggaagc caggcggcgg cggcaggagc agagcccatg gaacccgaga   2220
gccggcctgg accctcggga atgaatgttg tacaggtggc tgaactgtat ccagaactga   2280
gacgcatttt gacaattaca gaggatgggc aggggctaaa gggggtaaag agggagcggg   2340
gggcttgtga ggctacagag gaggctagga atctagcttt tagcttaatg accagacacc   2400
gtcctgagtg tattactttt caacagatca aggataattg cgctaatgag cttgatctgc   2460
tggcgcagaa gtattccata gagcagctga ccacttactg gctgcagcca ggggatgatt   2520
ttgaggaggc tattagggta tatgcaaagg tggcacttag gccagattgc aagtacaaga   2580
tcagcaaact tgtaaatatc aggaattgtt gctacatttc tgggaacggg gccgaggtgg   2640
agatagatac ggaggatagg gtggccttta gatgtagcat gataaatatg tggccggggg   2700
tgcttggcat ggacggggtg gttattatga atgtaaggtt tactggcccc aattttagcg   2760
gtacggtttt cctggccaat accaacctta tcctacacgg tgtaagcttc tatgggttta   2820
acaatacctg tgtggaagcc tggaccgatg taagggttcg gggctgtgcc ttttactgct   2880
gctggaaggg ggtggtgtgt cgccccaaaa gcagggcttc aattaagaaa tgcctctttg   2940
aaaggtgtac cttgggtatc ctgtctgagg gtaactccag ggtgcgccac aatgtggcct   3000
ccgactgtgt ttgcttcatg ctagtgaaaa gcgtggctgt gattaagcat aacatggtat   3060
gtggcaactg cgaggacagg gcctctcaga tgctgacctg ctcggacggc aactgtcacc   3120
```

| | |
|---|---|
| tgctgaagac cattcacgta gccagccact ctcgcaaggc ctggccagtg tttgagcata | 3180 |
| acatactgac ccgctgttcc ttgcatttgg gtaacaggag gggggtgttc ctaccttacc | 3240 |
| aatgcaattt gagtcacact aagatattgc ttgagcccga gagcatgtcc aaggtgaacc | 3300 |
| tgaacggggt gtttgacatg accatgaaga tctggaaggt gctgaggtac gatgagaccc | 3360 |
| gcaccaggtg cagaccctgc gagtgtggcg gtaaacatat taggaaccag cctgtgatgc | 3420 |
| tggatgtgac cgaggagctg aggcccgatc acttggtgct ggcctgcacc cgcgctgagt | 3480 |
| ttggctctag cgatgaagat acagattgag gtactgaaat gtgtgggcgt ggcttaaggg | 3540 |
| tgggaaagaa tatataaggt gggggtctta tgtagttttg tatctgtttt gcagcagccg | 3600 |
| ccgccgccat gagcaccaac tcgtttgatg aagcattgt gagctcatat ttgacaacgc | 3660 |
| gcatgccccc atgggccggg gtgcgtcaga atgtgatggg ctccagcatt gatggtcgcc | 3720 |
| ccgtcctgcc cgcaaactct actaccttga cctacgagac cgtgtctgga acgccgttgg | 3780 |
| agactgcagc ctccgccgcc gcttcagccg ctgcagccac cgcccgcggg attgtgactg | 3840 |
| actttgcttt cctgagcccg cttgcaagca gtgcagcttc ccgttcatcc gcccgcgatg | 3900 |
| acaagttgac ggctcttttg gcacaattgg attctttgac ccgggaactt aatgtcgttt | 3960 |
| ctcagcagct gttggatctg cgccagcagg tttctgccct gaaggcttcc tcccctccca | 4020 |
| atgcggttta aaacataaat aaaaaaccag actctgtttg gatttggatc aagcaagtgt | 4080 |
| cttgctgtct ttatttaggg gttttgcgcg cgcggtaggc ccgggaccag cggtctcggt | 4140 |
| cgttgagggt cctgtgtatt ttttccagga cgtggtaaag gtgactctgg atgttcagat | 4200 |
| acatgggcat aagcccgtct ctggggtgga ggtagcacca ctgcagagct tcatgctgcg | 4260 |
| gggtggtgtt gtagatgatc cagtcgtagc aggagcgctg ggcgtggtgc ctaaaaatgt | 4320 |
| ctttcagtag caagctgatt gcca | 4344 |

<210> SEQ ID NO 2
<211> LENGTH: 3018
<212> TYPE: DNA
<213> ORGANISM: Artificial
<220> FEATURE:
<223> OTHER INFORMATION: Synthetic primer
<220> FEATURE:
<223> OTHER INFORMATION: 505-3522 Ad5

<400> SEQUENCE: 2

| | |
|---|---|
| gagtgccagc gagtagagtt ttctcctccg agccgctccg acaccgggac tgaaaatgag | 60 |
| acatattatc tgccacggag gtgttattac cgaagaaatg gccgcagtc ttttggacca | 120 |
| gctgatcgaa gaggtactgg ctgataatct tccacctcct agccattttg aaccacctac | 180 |
| ccttcacgaa ctgtatgatt tagacgtgac ggccccgaa gatcccaacg aggaggcggt | 240 |
| ttcgcagatt tttcccgact ctgtaatgtt ggcggtgcag gaagggattg acttactcac | 300 |
| ttttcgccg gcgcccggtt ctccggagcc gcctcacctt tcccggcagc ccgagcagcc | 360 |
| ggagcagaga gccttgggtc cggtttctat gccaaacctt gtaccggagg tgatcgatct | 420 |
| tacctgccac gaggctggct ttccacccag tgacgacgag gatgaagagg gtgaggagtt | 480 |
| tgtgttagat tatgtggagc accccgggca cggttgcagg tcttgtcatt atcaccggag | 540 |
| gaatacgggg gacccagata ttatgtgttc gctttgctat atgaggacct gtggcatgtt | 600 |
| tgtctacagt aagtgaaaat tatgggcagt gggtgataga gtggtgggtt tggtgtggta | 660 |
| atttttttt taatttttac agttttgtgg tttaagaat tttgtattgt gatttttta | 720 |

```
aaaggtcctg tgtctgaacc tgagcctgag cccgagccag aaccggagcc tgcaagacct      780
acccgccgtc ctaaaatggc gcctgctatc ctgagacgcc cgacatcacc tgtgtctaga      840
gaatgcaata gtagtacgga tagctgtgac tccggtcctt ctaacacacc tcctgagata      900
cacccggtgg tccgctgtg ccccattaaa ccagttgccg tgagagttgg tgggcgtcgc       960
caggctgtgg aatgtatcga ggacttgctt aacgagcctg ggcaacccttt ggacttgagc    1020
tgtaaacgcc ccaggccata aggtgtaaac ctgtgattgc gtgtgtggtt aacgcctttg     1080
tttgctgaat gagttgatgt aagtttaata aagggtgaga taatgtttaa cttgcatggc     1140
gtgttaaatg gggcggggct taaagggtat ataatgcgcc gtgggctaat cttggttaca     1200
tctgacctca tggaggcttg ggagtgtttg aagatttttt ctgctgtgcg taacttgctg     1260
gaacagagct ctaacagtac ctcttggttt tggaggtttc tgtggggctc atcccaggca     1320
aagttagtct gcagaattaa ggaggattac aagtgggaat ttgaagagct tttgaaatcc     1380
tgtggtgagc tgtttgattc tttgaatctg ggtcaccagg cgcttttcca agagaaggtc     1440
atcaagactt tggatttttc cacaccgggg gcgcgctgcgg ctgctgttgc ttttttgagt    1500
tttataaagg ataaatggag cgaagaaacc catctgagcg gggggtacct gctggatttt     1560
ctggccatgc atctgtggag agcggttgtg agacacaaga atcgcctgct actgttgtct     1620
tccgtccgcc cggcgataat accgacggag gagcagcagc agcagcagga ggaagccagg     1680
cggcggcgga aggagcagag cccatggaac ccgagagccg gcctggaccc tcgggaatga    1740
atgttgtaca ggtggctgaa ctgtatccag aactgagacg cattttgaca attacagagg     1800
atgggcaggg gctaaagggg gtaaagaggg agcgggggc ttgtgaggct acagaggagg     1860
ctaggaatct agcttttagc ttaatgacca gacaccgtcc tgagtgtatt actttcaac     1920
agatcaagga taattgcgct aatgagcttg atctgctggc gcagaagtat tccatagagc     1980
agctgaccac ttactggctg cagccagggg atgattttga ggaggctatt agggtatatg     2040
caaaggtggc acttaggcca gattgcaagt acaagatcag caaacttgta aatatcagga     2100
attgttgcta catttctggg aacggggccg aggtggagat agatacggag gatagggtgg     2160
cctttagatg tagcatgata aatatgtggc cggggtgct tggcatggac ggggtggtta      2220
ttatgaatgt aaggtttact ggccccaatt ttagcggtac ggttttcctg gccaatacca     2280
acctatcct acacggtgta agcttctatg ggtttaacaa tacctgtgtg aagcctgga      2340
ccgatgtaag ggttcggggc tgtgcctttt actgctgctg aaggggggtg gtgtgtcgcc    2400
ccaaaagcag ggcttcaatt aagaaatgcc tcttgaaag gtgtaccttg ggtatcctgt     2460
ctgagggtaa ctccagggtg cgccacaatg tggcctccga ctgtggttgc ttcatgctag    2520
tgaaaagcgt ggctgtgatt aagcataaca tggtatgtgg caactgcgag acagggcct    2580
ctcagatgct gacctgctcg gacggcaact gtcacctgct gaagaccatt cacgtagcca    2640
gccactctcg caaggcctgg ccagtgtttg agcataacat actgacccgc tgttccttgc    2700
atttgggtaa caggaggggg gtgttcctac cttaccaatg caatttgagt cacactaaga    2760
tattgcttga gcccgagagc atgtccaagg tgaacctgaa cggggtgttt gacatgacca    2820
tgaagatctg gaaggtgctg aggtacgatg agacccgcac caggtgcaga ccctgcgagt    2880
gtggcggtaa acatattagg aaccagcctg tgatgctgga tgtgaccgag gagctgaggc    2940
ccgatcactt ggtgctggcc tgcacccgcg ctgagtttgg ctctagcgat gaagatacag    3000
attgaggtac tgaaatgt                                                  3018
```

<210> SEQ ID NO 3
<211> LENGTH: 3575
<212> TYPE: DNA
<213> ORGANISM: Artificial
<220> FEATURE:
<223> OTHER INFORMATION: Synthetic primer
<220> FEATURE:
<223> OTHER INFORMATION: 505-4079 Ad5

<400> SEQUENCE: 3

```
gagtgccagc gagtagagtt ttctcctccg agccgctccg acaccgggac tgaaaatgag     60
acatattatc tgccacggag gtgttattac cgaagaaatg gccgccagtc ttttggacca    120
gctgatcgaa gaggtactgg ctgataatct tccacctcct agccattttg aaccacctac    180
ccttcacgaa ctgtatgatt tagacgtgac ggccccgaa gatcccaacg aggaggcggt    240
ttcgcagatt tttcccgact ctgtaatgtt ggcggtgcag aagggattg acttactcac    300
ttttccgccg gcgcccggtt ctccggagcc gcctcacctt tcccggcagc ccgagcagcc    360
ggagcagaga gccttgggtc cggtttctat gccaaacctt gtaccggagg tgatcgatct    420
tacctgccac gaggctggct ttccacccag tgacgacgag gatgaagagg gtgaggagtt    480
tgtgttagat tatgtggagc accccggca cggttgcagg tcttgtcatt atcaccggag    540
gaatacgggg gacccagata ttatgtgttc gctttgctat atgaggacct gtggcatgtt    600
tgtctacagt aagtgaaaat tatgggcagt gggtgataga gtggtgggtt tggtgtggta    660
atttttttt taatttttac agttttgtgg tttaaagaat tttgtattgt gatttttta    720
aaaggtcctg tgtctgaacc tgagcctgag cccgagccag aaccggagcc tgcaagacct    780
acccgccgtc ctaaaatggc gcctgctatc ctgagacgcc cgacatcacc tgtgtctaga    840
gaatgcaata gtagtacgga tagctgtgac tccggtcctt ctaacacacc tcctgagata    900
cacccggtgg tcccgctgtg ccccattaaa ccagttgccg tgagagttgg tgggcgtcgc    960
caggctgtgg aatgtatcga ggacttgctt aacgagcctg gcaacctttt ggacttgagc   1020
tgtaaacgcc ccaggccata aggtgtaaac ctgtgattgc gtgtgtggtt aacgcctttg   1080
tttgctgaat gagttgatgt aagtttaata aagggtgaga taatgtttaa cttgcatggc   1140
gtgttaaatg gggcggggct aaagggtat ataatgcgcc gtgggctaat cttggttaca   1200
tctgacctca tggaggcttg ggagtgtttg gaagattttt ctgctgtgcg taacttgctg   1260
gaacagagct ctaacagtac ctcttggttt tggaggtttc tgtggggctc atcccaggca   1320
aagttagtct gcagaattaa ggaggattac aagtgggaat ttgaagagct tttgaaatcc   1380
tgtggtgagc tgtttgattc tttgaatctg ggtcaccagg cgcttttcca agagaaggtc   1440
atcaagactt tggattttc cacaccgggg cgcgctgcgg ctgctgttgc ttttttgagt   1500
tttataaagg ataaatggag cgaagaaacc catctgagcg gggggtacct gctggatttt   1560
ctggccatgc atctgtggag agcggttgtg agacacaaga atcgcctgct actgttgtct   1620
tccgtccgcc cggcgataat accgacggag gagcagcagc agcagcagga ggaagccagg   1680
cggcggcggc aggagcagag cccatggaac ccgagagccg gcctggaccc tcgggaatga   1740
atgttgtaca ggtggctgaa ctgtatccag aactgagacg cattttgaca attacagagg   1800
atgggcaggg gctaaagggg gtaaagaggg agcgggggc ttgtgaggct acagaggagg   1860
ctaggaatct agcttttagc ttaatgacca gacaccgtcc tgagtgtatt acttttcaac   1920
agatcaagga taattgcgct aatgagcttg atctgctggc gcagaagtat ccatagagc   1980
agctgaccac ttactggctg cagccagggg atgatttga ggaggctatt agggtatatg   2040
```

```
caaaggtggc acttaggcca gattgcaagt acaagatcag caaacttgta aatatcagga      2100
attgttgcta catttctggg aacggggccg aggtggagat agatacggag gatagggtgg      2160
cctttagatg tagcatgata aatatgtggc cgggggtgct tggcatggac ggggtggtta      2220
ttatgaatgt aaggtttact ggccccaatt ttagcggtac ggttttcctg gccaatacca      2280
accttatcct acacggtgta agcttctatg ggtttaacaa tacctgtgtg aagcctgga       2340 ccgatgtaag ggttcgggc tgtgcctttt actgctgctg aagggggtg gtgtgtcgcc       2400 ccaaaagcag ggcttcaatt aagaaatgcc tctttgaaag gtgtaccttg ggtatcctgt      2460
ctgagggtaa ctccagggtg cgccacaatg tggcctccga ctgtggttgc ttcatgctag      2520
tgaaaagcgt ggctgtgatt aagcataaca tggtatgtgg caactgcgag acagggcct      2580 ctcagatgct gacctgctcg gacggcaact gtcacctgct gaagaccatt cacgtagcca     2640
gccactctcg caaggcctgg ccagtgtttg agcataacat actgacccgc tgttccttgc     2700
atttgggtaa caggaggggg gtgttcctac cttaccaatg caatttgagt cacactaaga     2760
tattgcttga gcccgagagc atgtccaagg tgaacctgaa cggggtgttt gacatgacca     2820
tgaagatctg gaaggtgctg aggtacgatg agacccgcac caggtgcaga ccctgcgagt     2880
gtggcggtaa acatattagg aaccagcctg tgatgctgga tgtgaccgag gagctgaggc     2940
ccgatcactt ggtgctggcc tgcacccgcg ctgagtttgg ctctagcgat aagatacag      3000 attgaggtac tgaaatgtgt gggcgtggct taagggtggg aaagaatata aaggtgggg      3060 gtcttatgta gttttgtatc tgttttgcag cagccgccgc cgccatgagc accaactcgt     3120
ttgatggaag cattgtgagc tcatatttga caacgcgcat gccccatgg gccggggtgc      3180 gtcagaatgt gatgggctcc agcattgatg gtcgccccgt cctgcccgca aactctacta     3240
ccttgaccta cgagaccgtg tctgaacgc cgttggagac tgcagcctcc gccgccgctt      3300
cagccgctgc agccaccgcc cgcgggattg tgactgactt tgctttcctg agcccgcttg     3360
caagcagtgc agcttcccgt tcatccgccc gcgatgacaa gttgacggct cttttggcac     3420
aattggattc tttgacccgg gaacttaatg tcgtttctca gcagctgttg gatctgcgcc     3480
agcaggtttc tgccctgaag gcttcctccc ctcccaatgc ggtttaaaac ataaataaaa     3540
aaccagactc tgtttggatt tggatcaagc aagtg                                3575

<210> SEQ ID NO 4
<211> LENGTH: 2499
<212> TYPE: DNA
<213> ORGANISM: Artificial
<220> FEATURE:
<223> OTHER INFORMATION: Synthetic primer
<220> FEATURE:
<223> OTHER INFORMATION: SV40 T-antigen

<400> SEQUENCE: 4
atcatggata aagttttaaa cagagaggaa tctttgcagc taatggacct tctaggtctt       60
gaaaggagtg cctgggggaa tattcctctg atgagaaagg catatttaaa aaaatgcaag     120
gagtttcatc ctgataaagg aggagatgaa gaaaaaatga gaaaatgaa tactctgtac      180 aagaaaatgg aagatggagt aaaatatgct catcaacctg actttggagg cttctgggat     240
gcaactgagg tatttgcttc ttccttaaat cctggtgttg atgcaatgta ctgcaaacaa    300
tggcctgagt gtgcaaagaa aatgtctgct aactgcatat gcttgctgtg cttactgagg    360
atgaagcatg aaaatagaaa attatacagg aaagatccac ttgtgtgggt tgattgctac    420
tgcttcgatt gctttagaat gtggtttgga cttgatcttt gtgaaggaac cttacttctg    480
```

```
tggtgtgaca taattggaca aactacctac agagatttaa agctctaagg taaatataaa    540 attttttaagt gtataatgtg ttaaactact gattctaatt gtttgtgtat tttagattcc    600
aacctatgga actgatgaat gggagcagtg gtggaatgcc tttaatgagg aaaacctgtt    660
ttgctcagaa gaaatgccat ctagtgatga tgaggctact gctgactctc aacattctac    720
tcctccaaaa aagaagagaa aggtagaaga ccccaaggac tttccttcag aattgctaag    780 tttttttgagt catgctgtgt ttagtaatag aactcttgct tgcttttgcta tttacaccac    840 aaaggaaaaa gctgcactgc tatacaagaa aattatggaa aaatattctg taacctttat    900
aagtaggcat aacagttata atcataacat actgtttttt cttactccac acaggcatag    960
agtgtctgct attaataact atgctcaaaa attgtgtacc tttagctttt taatttgtaa    1020 agggggttaat aaggaatatt tgatgtatag tgccttgact agagatccat tttctgttat    1080
tgaggaaagt ttgccaggtg ggttaaagga gcatgatttt aatccagaag aagcagagga    1140
aactaaacaa gtgtcctgga agcttgtaac agagtatgca atggaaacaa aatgtgatga    1200
tgtgttgtta ttgcttggga tgtacttgga atttcagtac agttttgaaa tgtgtttaaa    1260
atgtattaaa aaagaacagc ccagccacta taagtaccat gaaaagcatt atgcaaatgc    1320
tgctatattt gctgacagca aaaaccaaaa aaccatatgc caacaggctg ttgatactgt    1380
tttagctaaa aagcggggttg atagcctaca attaactaga gaacaaatgt taacaaacag    1440
atttaatgat cttttggata ggatggatat aatgtttggt tctacaggct ctgctgacat    1500
agaagaatgg atggctggag ttgcttggct acactgtttg ttgcccaaaa tggattcagt    1560
ggtgtatgac tttttaaaat gcatggtgta caacattcct aaaaaaagat actggctgtt    1620
taaaggacca attgatagtg gtaaaactac attagcagct gctttgcttg aattatgtgg    1680
ggggaaagct ttaaatgtta atttgcccctt ggacaggctg aactttgagc taggagtagc    1740
tattgaccag ttttttagtag ttttttgagga tgtaaagggc actggagggg agtccagaga    1800
tttgccttca ggtcagggaa ttaataacct ggacaattta agggattatt tggatggcag    1860
tgttaaggta aacttagaaa agaaacacct aaataaaaga actcaaatat ttccccctgg    1920
aatagtcacc atgaatgagt acagtgtgcc taaaacactg caggccagat ttgtaaaaca    1980
aatagatttt aggcccaaag attatttaaa gcattgcctg gaacgcagtg agtttttgtt    2040
agaaaagaga ataattcaaa gtggcattgc tttgcttctt atgttaattt ggtacagacc    2100
tgtggctgag tttgctcaaa gtattcagag cagaattgtg gagtggaaag agagattgga    2160
caaagagttt agttttgtcag tgtatcaaaa aatgaagttt aatgtggcta tgggaattgg    2220
agttttagat tggctaagaa acagtgatga tgatgatgaa gacagccagg aaaaatgctga    2280 taaaaatgaa gatggtgggg agaagaacat ggaagactca gggcatgaaa caggcattga    2340
ttcacagtcc caaggctcat ttcaggcccc tcagtcctca cagtctgttc atgatcataa    2400
tcagccatac cacatttgta gaggttttac ttgctttaaa aaacctccca cacctccccc    2460
tgaacctgaa acataaggat ccagcgatcc gcctgaatt    2499
```

<210> SEQ ID NO 5
<211> LENGTH: 523
<212> TYPE: DNA
<213> ORGANISM: Artificial
<220> FEATURE:
<223> OTHER INFORMATION: Synthetic primer
<220> FEATURE:
<223> OTHER INFORMATION: CMV promoter

```
<400> SEQUENCE: 5
gttacataac ttacggtaaa tggcccgcct ggctgaccgc ccaacgaccc ccgcccattg      60
acgtcaataa tgacgtatgt tcccatagta acgccaatag ggactttcca ttgacgtcaa     120
tgggtggagt atttacggta aactgcccac ttggcagtac atcaagtgta tcatatgcca     180
agtacgcccc ctattgacgt caatgacggt aaatggcccg cctggcatta tgcccagtac     240
atgaccttat gggactttcc tacttggcag tacatctacg tattagtcat cgctattacc     300
atggtgatgc ggttttggca gtacatcaat gggcgtggat agcggtttga ctcacgggga     360
tttccaagtc tccacccccat tgacgtcaat gggagtttgt tttggcacca aaatcaacgg    420
gactttccaa aatgtcgtaa caactccgcc ccattgacgc aaatgggcgg taggcgtgta     480
cggtgggagg tctatataag cagagctcgt ttagtgaacc gtc                       523

<210> SEQ ID NO 6
<211> LENGTH: 97
<212> TYPE: DNA
<213> ORGANISM: Artificial
<220> FEATURE:
<223> OTHER INFORMATION: Synthetic primer
<220> FEATURE:
<223> OTHER INFORMATION: SV40 SD/SA (intron)

<400> SEQUENCE: 6
taagtttagt cttttgtct tttatttcag gtcccggatc cggtggtggt gcaaatcaaa       60
gaactgctcc tcagtggatg ttgcctttac ttctagg                              97

<210> SEQ ID NO 7
<211> LENGTH: 147
<212> TYPE: DNA
<213> ORGANISM: Artificial
<220> FEATURE:
<223> OTHER INFORMATION: Synthetic primer
<220> FEATURE:
<223> OTHER INFORMATION: SV40 polyA (T-antigen)

<400> SEQUENCE: 7
ggggatccag acatgataag atacattgat gagtttggac aaaccacaac tagaatgcag      60
tgaaaaaaat gctttatttg tgaaatttgt gatgctattg ctttatttgt aaccattata    120
agctgcaata aacaagttaa caacaac                                         147

<210> SEQ ID NO 8
<211> LENGTH: 1926
<212> TYPE: DNA
<213> ORGANISM: Artificial
<220> FEATURE:
<223> OTHER INFORMATION: Synthetic primer
<220> FEATURE:
<223> OTHER INFORMATION: EBNA-1

<400> SEQUENCE: 8
atgtctgacg aggggccagg tacaggacct ggaaatggcc taggagagaa gggagacaca      60
tctggaccag aaggctccgg cggcagtgga cctcaaagaa gaggggtga taaccatgga     120 cgaggacggg gaagaggacg aggacgagga ggcggaagac caggagcccc gggcggctca     180
ggatcagggc caagacatag agatggtgtc cggagacccc aaaaacgtcc aagttgcatt     240
ggctgcaaag ggacccacgg tggaacagga gcaggagcag gagcgggagg gcaggagca      300 ggaggggcag gagcaggagg aggggcagga gcaggaggag gggcaggagg ggcaggaggg     360
gcaggagggg caggagcagg aggagggca ggagcaggag gaggggcagg aggggcagga     420
```

```
ggggcaggag caggaggagg ggcaggagca ggaggagggg caggaggggc aggagcagga      480
ggaggggcag gaggggcagg aggggcagga gcaggaggag gggcaggagc aggaggaggg      540
gcaggagggg caggagcagg aggaggggca ggaggggcag gaggggcagg agcaggagga      600
ggggcaggag caggaggggc aggaggggca ggaggggcag gagcaggagg ggcaggagca      660
ggaggagggg caggaggggc aggaggggca ggagcaggag gggcaggagc aggaggggca      720
ggagcaggag gggcaggagc aggaggggca ggaggggcag gagcaggagg ggcaggaggg      780
gcaggagcag gaggggcagg aggggcagga gcaggaggag gggcaggagg ggcaggagca      840
ggaggagggg caggaggggc aggagcagga ggggcaggag gggcaggagc aggaggggca      900
ggaggggcag gagcaggagg ggcaggaggg gcaggagcag gaggagggc aggagcagga      960 ggggcaggag caggaggtgg aggccggggt cgaggaggca gtggaggccg gggtcgagga     1020
ggtagtggag gccggggtcg aggaggtagt ggaggccgcc ggggtagagg acgtgaaaga     1080
gccagggggg gaagtcgtga aagagccagg gggagaggtc gtggacgtgg agaaaagagg     1140
cccaggagtc ccagtagtca gtcatcatca tccgggtctc caccgcgcag gcccccctcca     1200 ggtagaaggc cattttttcca ccctgtaggg gaagccgatt attttgaata ccaccaagaa     1260
ggtggcccag atggtgagcc tgacgtgccc ccgggagcga tagagcaggg ccccgcagat     1320
gacccaggag aaggcccaag cactggaccc cggggtcagg gtgatggagg caggcgcaaa     1380
aaaggagggt ggtttggaaa gcatcgtggt caaggaggtt ccaacccgaa atttgagaac     1440
attgcagaag gtttaagagc tctcctggct aggagtcacg tagaaaggac taccgacgaa     1500
ggaacttggg tcgccggtgt gttcgtatat ggaggtagta agacctccct ttacaaccta     1560
aggcgaggaa ctgcccttgc tattccacaa tgtcgtctta caccattgag tcgtctcccc     1620
tttggaatgg cccctggacc cggcccacaa cctggcccgc taagggagtc cattgtctgt     1680
tatttcatgg tcttttttaca aactcatata tttgctgagg ttttgaagga tgcgattaag     1740
gaccttgtta tgacaaagcc cgctcctacc tgcaatatca gggtgactgt gtgcagcttt     1800
gacgatggag tagatttgcc tccctggttt ccacctatgg tggaagggc tgccgcggag     1860 ggtgatgacg gagatgacgg agatgaagga ggtgatggag atgagggtga ggaagggcag     1920
gagtga                                                                1926

<210> SEQ ID NO 9
<211> LENGTH: 29
<212> TYPE: DNA
<213> ORGANISM: Artificial
<220> FEATURE:
<223> OTHER INFORMATION: Synthetic primer

<400> SEQUENCE: 9
ccggaattct ttgcaaaagc ctaggcctc                                          29

<210> SEQ ID NO 10
<211> LENGTH: 29
<212> TYPE: DNA
```

```
<213> ORGANISM: Artificial
<220> FEATURE:
<223> OTHER INFORMATION: Synthetic primer

<400> SEQUENCE: 10
ccggaattct gaggcggaaa gaaccagct                                              29

<210> SEQ ID NO 11
<211> LENGTH: 359
<212> TYPE: DNA
<213> ORGANISM: Artificial
<220> FEATURE:
<223> OTHER INFORMATION: Synthetic primer
<220> FEATURE:
<223> OTHER INFORMATION: SV40 ori

<400> SEQUENCE: 11
tttgcaaaag cctaggcctc caaaaaagcc tcctcactac ttctggaata gctcagaggc            60
cgaggcggcc tcggcctctg cataaataaa aaaaattagt cagccatggg gcggagaatg          120
ggcggaactg gcggagtta ggggcgggat gggcggagtt aggggcggga ctatggttgc           180
tgactaattg agatgcatgc tttgcatact tctgcctgct ggggagcctg ggacttttcc          240
acacctggtt gctgactaat tgagatgcat gctttgcata cttctgcctg ctggggagcc          300
tggggacttt ccacacccta actgacacac attccacagc tggttctttc cgcctcaca          359

<210> SEQ ID NO 12
<211> LENGTH: 1378
<212> TYPE: DNA
<213> ORGANISM: Artificial
<220> FEATURE:
<223> OTHER INFORMATION: Synthetic primer
<220> FEATURE:
<223> OTHER INFORMATION: hAAT

<400> SEQUENCE: 12
attctgcagg ggggggggg ggctgggaca gtgaatcgac aatgccgtct tctgtctcgt            60
ggggcatcct cctgctggca ggcctgtgct gcctggtccc tgtctccctg ctgaggatc           120 cccagggaga tgctgcccag aagacagata catcccacca tgatcaggat cacccaacct          180
tcaacaagat caccccaac ctggctgagt tcgccttcag cctataccgc cagctggcac           240
accagtccaa cagcaccaat atcttcttct ccccagtgag catcgctaca gcctttgcaa          300
tgctctccct ggggaccaag gctgacactc acgatgaaat cctggagggc tgaatttca           360 acctcacgga gattccggag gctcagatcc atgaaggctt ccaggaactc tccgtaccc          420 tcaaccagcc agacagccag ctccagctga ccaccggcaa tggcctgttc ctcagcgagg         480
gcctgaagct agtggataag tttttggagg atgttaaaaa gttgtaccac tcagaagcct         540
tcactgtcaa cttcggggac accgaagagg ccaagaaaca gatcaacgat tacgtggaga         600
agggtactca agggaaaatt gtggatttgg tcaaggagct tgacagagac acagttttg          660 ctctggtgaa ttacatcttc tttaaaggca atgggagag accctttgaa gtcaaggaca          720
ccgaggaaga ggacttccac gtggaccagg tgaccaccgt gaaggtgcct atgatgaagc         780
gtttaggcat gtttaacatc cagcactgta agaagctgtc cagctgggtg ctgctgatga         840
aatacctggg caatgccacc gccatcttct tcctgcctga tgagggaaaa ctacagcacc          900
tggaaaatga actcacccac gatatcatca ccagttcct ggaaaatgaa gacagaaggt          960
ctgccagctt acatttaccc aaactgtcca ttactggaac ctatgatctg aagagcgtcc        1020
tgggtcaact gggcatcact aaggtcttca gcaatgggc tgacctctcc gggtcacag         1080
```

```
aggaggcacc cctgaagctc tccaaggccg tgcataaggc tgtgctgacc atcgacgaga    1140
aagggactga agctgctggg gccatgtttt tagaggccat acccatgtct atcccccccg    1200
aggtcaagtt caacaaaccc tttgtcttct taatgattga acaaaatacc aagtctcccc    1260
tcttcatggg aaaagtggtg aatcccaccc aaaaataact gcctctcgct cctcaacccc    1320
tcccctccat ccctggcccc ctccctggat gacattaaag aagggttgag ctggattg     1378
```